(12) United States Patent
Patel

(10) Patent No.: US 12,123,858 B2
(45) Date of Patent: Oct. 22, 2024

(54) TIME-TEMPERATURE INDICATOR BASED ON INCREASED THERMAL REACTIVITY OF A DIACETYLENE UPON MELT RECRYSTALLIZATION

(71) Applicant: JP LABORATORIES, Middlesex, NJ (US)

(72) Inventor: Gordhanbhai Patel, Somerset, NJ (US)

(73) Assignee: JP Laboratories, Inc., Middlesex, NJ (US)

( * ) Notice: Subject to any disclaimer, the term of this patent is extended or adjusted under 35 U.S.C. 154(b) by 25 days.

(21) Appl. No.: 16/098,685

(22) PCT Filed: May 1, 2017

(86) PCT No.: PCT/US2017/030390
§ 371 (c)(1),
(2) Date: Nov. 2, 2018

(87) PCT Pub. No.: WO2017/192444
PCT Pub. Date: Nov. 9, 2017

(65) Prior Publication Data
US 2019/0137462 A1  May 9, 2019

Related U.S. Application Data

(60) Provisional application No. 62/467,413, filed on Mar. 6, 2017, provisional application No. 62/411,093, filed
(Continued)

(51) Int. Cl.
*G01N 31/22*  (2006.01)
*B41M 3/14*  (2006.01)
(Continued)

(52) U.S. Cl.
CPC ........... *G01N 31/229* (2013.01); *B41M 3/142* (2013.01); *B41M 5/28* (2013.01); *B41M 5/284* (2013.01);
(Continued)

(58) Field of Classification Search
CPC ....... G01N 31/229; B41M 3/142; B41M 5/28; B41M 5/284; C07C 271/12; G01K 3/04; G01K 11/16
See application file for complete search history.

(56) References Cited

U.S. PATENT DOCUMENTS 4,189,399 A * 2/1980 Patel ............... C07C 309/66
250/474.1
4,208,186 A * 6/1980 Patel ............... G01N 31/229
436/2
(Continued)

OTHER PUBLICATIONS

ISA/US; International Search Report and Written Opinion prepared for PCT/US2017/030390; Date mailed: Aug. 1, 2017.

*Primary Examiner* — Nathaniel T Woodward
*Assistant Examiner* — Philip L Cotey
(74) *Attorney, Agent, or Firm* — Joseph T. Guy; Patent Filing Specialist Inc.

(57) ABSTRACT

This application relates to a time-temperature indicator based on increased thermal reactivity of a diacetylene upon melt recrystallization and a method of making it. A diacetylene is crystallized into a low thermal reactivity phase from a solvent system and converted into a higher thermal reactivity phase and low sensitivity to UV light by melt re-crystallization.

24 Claims, 8 Drawing Sheets

Related U.S. Application Data on Oct. 21, 2016, provisional application No. 62/330,952, filed on May 3, 2016.

(51) Int. Cl.
  B41M 5/28 (2006.01)
  C07C 271/12 (2006.01)
  G01K 3/04 (2006.01)
  G01K 11/16 (2021.01)

(52) U.S. Cl.
  CPC .............. *C07C 271/12* (2013.01); *G01K 3/04* (2013.01); *G01K 11/16* (2013.01)

(56) References Cited

U.S. PATENT DOCUMENTS

| | | | | |
|---|---|---|---|---|
| 4,228,126 A * | 10/1980 | Patel | ........................ | G01K 3/04 436/2 |
| 4,276,190 A * | 6/1981 | Patel | ..................... | G01N 31/229 374/102 |
| 4,278,561 A * | 7/1981 | Yee | ....................... | G01N 31/229 374/102 |
| 4,298,348 A * | 11/1981 | Ivory | .................... | G01N 31/229 116/207 |
| 4,344,909 A * | 8/1982 | De Blauwe | ............. | B29C 61/06 53/442 |
| 4,578,689 A * | 3/1986 | Spencer | ............. | G06K 15/1219 347/132 |
| 4,734,355 A * | 3/1988 | Lewis | ..................... | G03F 7/025 430/296 |
| 4,892,677 A * | 1/1990 | Preziosi | ............... | G01N 31/229 374/161 |
| 5,095,134 A * | 3/1992 | Liu | ........................ | C07C 69/007 560/24 |
| 5,672,465 A * | 9/1997 | Patel | ....................... | G03F 7/025 430/374 |
| 6,524,000 B1 * | 2/2003 | Roth | ........................ | B41M 3/14 374/102 |
| 2005/0037498 A1 * | 2/2005 | Ribi | ..................... | G01N 31/229 436/2 |
| 2005/0208290 A1 * | 9/2005 | Patel | ........................ | G01T 1/06 428/323 |
| 2006/0145091 A1 * | 7/2006 | Patel | ........................ | G01T 1/04 250/474.1 |
| 2006/0223898 A1 * | 10/2006 | Economy | ............... | C08G 61/02 521/61 |
| 2007/0158624 A1 * | 7/2007 | Weder | ...................... | C09K 9/02 252/582 |
| 2009/0050049 A1 * | 2/2009 | Craig | ........................ | G01K 1/02 374/E11.006 |
| 2009/0128345 A1 * | 5/2009 | Patel | ........................ | G01J 1/50 340/600 |
| 2011/0086995 A1 * | 4/2011 | Castillo Martinez | ........................ | C07C 275/20 526/285 |
| 2011/0104603 A1 * | 5/2011 | Yu | ........................ | G03G 5/0564 430/96 |
| 2012/0021363 A1 * | 1/2012 | Jarvis | ...................... | G03F 7/105 430/374 |
| 2012/0045837 A1 * | 2/2012 | Prusik | .................... | C09D 11/50 436/2 |
| 2012/0205591 A1 * | 8/2012 | Patel | ........................ | G01T 1/04 156/60 |
| 2013/0324684 A1 * | 12/2013 | Arajawa | ............ | C09K 19/3823 526/263 |
| 2014/0038101 A1 * | 2/2014 | Coyle | ................... | G03G 9/0821 430/137.1 |
| 2015/0152852 A1 * | 6/2015 | Li | ........................... | D02G 3/448 60/527 |
| 2015/0308901 A1 * | 10/2015 | Salman | ..................... | G01K 3/04 374/102 |
| 2016/0290859 A1 * | 10/2016 | Yu | ............................. | C08J 7/043 |

* cited by examiner

TIME-TEMPERATURE INDICATOR BASED ON INCREASED THERMAL REACTIVITY OF A DIACETYLENE UPON MELT RECRYSTALLIZATION

This application claims the benefit of U.S. Provisional Application Nos. 62/330,952, filed May 3, 2016, 62/411,093, filed Oct. 12, 2016 and 62/467,413, filed Mar. 6, 2017.

FIELD OF THE INVENTION

The present invention relates to a time-temperature indicator based on increased thermal reactivity and low UV reactivity of a diacetylene upon melt recrystallization and a method of making it.

BACKGROUND OF INVENTION

Diacetylenes (R—C≡C—C≡C—R, where R is a substituent group, DA) are colorless solids and are known to polymerize in the solid state to a highly-colored polymer upon thermal annealing or exposure to ionizing radiation. A number of active and inactive diacetylenes are reported in the literature, for example that listed by Enkelmann in Advances in Polymer Science; vol. 63, pp91-136 (1984). Diacetylenes are used as time-temperature indicators (TTI) for monitoring thermal degradation of perishables and as radiation dosimeters. Diacetylenes used for most of the application are always active, i.e., they polymerize upon thermal annealing, ionizing radiation and many other stimuli. Diacetylenes, when crystallized from a solvent or melt, do not always crystallize into an active phase. Many diacetylenes crystallize into an inactive phase. Some diacetylenes crystallize into more than one phases and each phase has different reactivity to radiation and heat. Some diacetylenes are very thermally reactive while others are very radiation reactive. The solvent used for crystallization and the method of crystallization often determines the crystallographic packing of the molecules and hence their reactivity. Some diacetylenes crystallize into an active phase when crystallized from a solvent and become inactive when crystallized from its melt and vice versa.

The concept of using an inactive diacetylene for TTI is disclosed in U.S. Pat. Nos. 4,208,186; 4,228,126; 4,276,190; 4,298,348 and 6,524,000. These patents disclose totally inactive diacetylenes listed in Table 1 below and their cocrystallized mixtures that can be converted from their inactive phases to active phases upon melting or upon exposure to a solvent, such as p-dioxane, dimethylformamide and pyridine or its vapor:

TABLE 1

Inactive diacetylenes.

1. 2,4-hexadiyn-1,6-diol bis(m-tolylurethane),
2. 2,4-hexadiyn-1,6-diol bis(o-chlorophenylurethane),
3. 2,4-hexadiyn-1,6-diol bis(o-methoxyphenylurethane),
4. 2,4-hexadiyn-1,6-diol bis(p-chlorophenylurethane),
5. 2,4-hexadiyn-1,6-diol bis(phenylurethane),
6. 2,4-hexadiyn-1,6-diol bis(p-methoxybenzene sulfonate),
7. 2,4-hexadiyn-1,6-diol bis(p-toluene sulfonate),
8. 2,4-hexadiyn-1,6-diol-bis(p-chlorobenzene sulfonate),
9. 2,4-hexadiyn-1,6-diol-bis(t-phenylazophenyl sulfonate),
10. 9-(N-carbazolyl)-5,7-nonadiyn-1-ol phenylurethane,
11. o,o'-diacetylenyldiphenyl glutarate.

The above (except the last two) are urethane and sulfonate derivatives of 2,4-hexadiyn-1,6-diol.

U.S. Pat. No. 6,524,000 discloses a method of making a time temperature indicator wherein an inactive diacetylene coated on a substrate is heated/melted with a direct thermal imaging apparatus for converting into an active phase.

The inactive TTI devices reported in the above patents are made by spray coating a solution of a diacetylene (with or without a binder, such as epoxy glue, lacquer or shellac) on a substrate or by dipping a substrate, such as a paper in the solution followed by evaporation of the solvent to crystallize the diacetylene in to an inactive phase. It is difficult to get fine crystals and crystals of uniform size by the methods disclosed in the above patents. It is also difficult to get uniform reproducible coating by spray or dip coating method.

A basic problem with diacetylene based TTI is their sensitivity to UV light. Even after four decades of development work, available diacetylene based TTI, such as those from Temptime Corporation (Morris Plains, NJ) are still very sensitive to UV light and hence users are asked to protect them from UV light. For example, a ten second exposure of VVM2 (which has UV protective film), a TTI of Temptime Corporation from a 4 watt 254 nm light at 5 cm distance, make the VVM2 TTI expire, i.e., diacetylene based TTI are readily tamperable. Any exposure of the TTI to UV light can give a false positive signal. The UV sensitivity limits the utility of diacetylene based TTI to limited number of perishables, such as vaccines which are not readily exposed to UV light. So far there is no report in the literature of a diacetylene based TTI which is not sensitive to UV light. Use of an active diacetylene or a diacetylene converted to an active phase from an inactive phase does not serve the purpose if it is still sensitive to UV light.

SUMMARY OF THE INVENTION

It has now been found that inactive diacetylenes can be used as TTI or radiation dosimeter if they can be activated by melt-recrystallization into an active phase. It has now been found that a coating of an inactive diacetylene in a binder heated to melt the diacetylene and cooled to a lower temperature is thermally active but it is not sensitive to UV light for all practical purposes. This totally unexpected discovery widens the utility of diacetylene based TTI to monitor shelf life of almost all perishables.

It has been found that the diacetylenes listed in Table 1 are truly inactive diacetylenes, i.e., they did not develop color even after storing them for one years at room temperature. However, for making an activatable TTI one does not need such totally inactive diacetylenes. An inactive diacetylene with an acceptably low thermal reactivity, e.g., no noticeable color development for a few days or a few weeks at room temperature which becomes active upon melt recrystallization can also be used to make a TTI.

None of the above patents disclose a method of making water and solvent based dispersion of an inactive diacetylene e.g., an ink of an inactive diacetylene by cooling hot solution of a diacetylene and a binder to a lower temperature so that the diacetylene crystallizes in to fine crystals of the diacetylene which are inactive.

Thus, in an aspect of the invention there is provided a precursor TTI device composed of a layer comprising a binder, an inactive DA and optionally a UV absorber and other additives on a substrate.

In another aspect of the invention there is provided a precursor TTI device composed of layer comprising at least a binder and an inactive DA wherein the binder does not get substantially dissolved, swollen or plasticized by the molten DA.

In another aspect of the invention there is provided a precursor TTI having a non-stick or releasing polymeric top layer.

In another aspect of the invention there is provided a precursor TTI having a non-stick or releasing layer of non-melting organic or inorganic nano or micron sized particles.

In another aspect of the invention there is provided a precursor TTI having a UV absorbing protective layer.

In another aspect of the invention there is provided a precursor TTI wherein at least one layer undergoes a visual or machine readable change including change in opaqueness, transparency, color or fluorescence when an inactive DA is melted.

In another aspect of the invention there is provided a precursor TTI having at least one color reference bar/chart for monitoring expiration of the device by matching its color with the color of the activated DA.

In another aspect of the invention there is provided a precursor TTI composed of a substrate, a layer composed on an inactive diacetylene in a binder and an additive, a protective layer, a color reference bar and a polymer having very high melting temperature non-tacky release layer.

In another aspect of the invention there is provided a TTI composed of a substrate and a layer composed of an active diacetylene generated from inactive diacetylene by melt recrystallization and a binder.

In another aspect of the invention there is provided a TTI composed of a substrate, a layer composed on an active diacetylene generated from inactive diacetylene by melt recrystallization, a binder and an additive.

In another aspect of the invention there is provided a TTI composed of a substrate, a layer composed on an active diacetylene generated from inactive diacetylene by melt recrystallization, a binder and an additive, a protective layer and a high temperature non-tacky release layer.

In another aspect of the invention there is provided a TTI wherein the additive depresses the melting point of the DA.

In another aspect of the invention there is provided a melt activated TTI which is not affected by UV light or has negligible effect of UV light In another aspect of the invention there is provided a melt-activated TTI which is not affected by humidity and UV light.

In another aspect of the invention there is provided a precursor TTI wherein an inactive DA in a binder is coated in form of a barcode or on a barcode.

In another aspect of the invention there is provided a precursor TTI wherein an additive is a heat stabilizer and/or a nucleating agent.

In another aspect of the invention there is provided a precursor TTI wherein a DA is crystallized into an inactive phase by cooling its solution of the DA with or without a binder.

In another aspect of the invention there is provided a precursor TTI having a shelf life of a week to ten years at room temperature without development of any noticeable color.

In another aspect of the invention there is provided a precursor TTI having a shelf life of a week to a few years under normal ambient conditions of heat, humidity and light without development of any noticeable color.

In another aspect of the invention there is provided a precursor TTI wherein fine particles of an inactive DA are prepared by milling it with or without additives and with or without a binder.

In another aspect of the invention there is provided a precursor TTI wherein fine particles of an inactive DA are prepared by low temperature (cryogenic) milling the DA with or without additives and with or without a binder.

In another aspect of the invention there is provided a precursor TTI wherein the diacetylene layer also contains fine particles of an opaque material, preferably white, such as micro or nano crystalline cellulose and/or nano or micron size inorganic materials, such as zinc oxide, titanium oxide and silica and a binder.

In another aspect of the invention there is provided a precursor TTI wherein the additive is a solid solvent for DA.

In another aspect of the invention there is provided a precursor TTI made by UV curing a mixture of inactive DA and a UV curing ink.

In another aspect of the invention there is provided a precursor TTI made by UV curing a mixture of inactive DA, a UV curing ink and cured with a UV light.

In another aspect of the invention there is provided a precursor TTI which is not affected by ambient conditions, such as heat, humidity and UV light.

In another aspect of the invention there is provided a precursor TTI composed of an inactive diacetylene, R—C≡C—C≡C—R, where R is selected from: $(CH_2)_b$—H; $(CH_2)_b$—OH; $(CH_2)_b$—OCONH—R1; $(CH_2)_b$—O—CO—R1; $(CH_2)_b$—O—R1; $(CH_2)_b$—COOH; $(CH_2)_b$—COOM; $(CH_2)_b$—$NH_2$; $(CH_2)_b$—CONHR1; $(CH_2)_b$—NHCONHR1; $(CH_2)_b$—CO—O—R1; where b=1-10, preferably 1-4, and R1 is substituted or unsubstituted alkyl or phenyl, and M is a cation, such as $Na^+$ or $(R1)_3N^+$ and their cocrystallized mixtures. The substituent group R1 is a alkyl or phenyl group, with or without substituted with one or more of —Cl, —Br, —I, F, —$NO_2$, alkyl, phenyl, alkoxy and phenoxy.

In another aspect of the invention there is provided a melt activated TTI composed of an active diacetylene, R—C≡C—C≡C—R, where R is selected from: $(CH_2)_b$—H; $(CH_2)_b$—OH; $(CH_2)_b$—OCONH—R1; $(CH_2)_b$—O—CO—R1; $(CH_2)_b$—O—R1; $(CH_2)_b$—COOH; $(CH_2)_b$—COOM; $(CH_2)_b$—$NH_2$; $(CH_2)_b$—CONHR1; $(CH_2)_b$—NHCONHR1; $(CH_2)_b$—CO—O—R1; where b=1-10, preferably 1-4, and R1 is substituted or unsubstituted alkyl or phenyl, and M is a cation, such as $Na^+$ or $(R1)_3N^+$ and their cocrystallized mixtures. The substituent group R1 is a alkyl or phenyl group, with or without substituted with one or more of —Cl, —Br, —I, F, —$NO_2$, alkyl, phenyl, alkoxy and phenoxy.

In another aspect of the invention there is provided a precursor TTI wherein the device is activated by heating rapidly to melt a DA (can be active or inactive) and cooling rapidly to crystallize the molten DA.

In another aspect of the invention there is provided a precursor TTI wherein the device is activated by heating it from room temperature to above the melting point of a DA in seconds or less than a second and cooled to room temperature or below from molten DA in seconds or less than a second.

In another aspect of the invention there is provided a precursor TTI wherein the DA is melted with a heating device followed by a cooling device.

In another aspect of the invention there is provided a precursor TTI wherein the DA is melted by passing over at least one heated device, such as a heated roller followed by crystallization of the molten DA by passing over a cooling device, such as a cooled roller.

In another aspect of the invention there is provided a precursor TTI wherein a DA is melted with infrared light from an IR lamp, IR laser, IR LED and/or induction heating.

In another aspect of the invention there is provided a precursor TTI which when activated by heating the TTI above the melting point of the DA becomes significantly inactive to UV light and is thermally active.

In another aspect of the invention there is provided a precursor TTI which when activated by heating it above the melting point of the DA, the device becomes significantly inactive to UV light.

In another aspect of the invention there is provided an active TTI wherein the DA is thermally and radiation active and the radiation reactivity is reduced by heating the active TTI above the melting point of the DA followed by cooling to a lower temperature.

In another aspect of the invention there is provided an active TTI made from melt crystallized diacetylene.

In another aspect of the invention there is provided an active TTI made from melt crystallized diacetylene which has lower radiation reactivity than that made from solution crystallized diacetylene.

In another aspect of the invention there is provided an active TTI made from melt crystallized diacetylene which is milled and dispersed in a binder.

In another aspect of the invention there is provided an active TTI made from melt crystallized diacetylene which is milled and dispersed in a binder.

In another aspect of the invention there is provided a TTI wherein the binder does not significantly affect properties of the TTI, e.g., does not form a solid solution with the DA.

In another aspect of the invention there is provided a precursor TTI wherein the TTI is a threshold TTI, i.e., gets activated if heated above a predetermined temperature.

In another aspect of the invention there is provided an active TTI wherein the TTI is a threshold TTI, i.e., becomes activated above a predetermined temperature.

In another aspect of the invention there is provided a precursor TTI wherein the diacetylene is made substantially inactive by rapid cooling from solution, by co-crystallizing with another diacetylene or by interaction with a binder or an additive which make the diacetylene inactive.

In another aspect of the invention there is provided a TTI made from its precursor wherein the rate of color development and activation energy are varied by varying the nature and concentration of diacetylene, co-crystallizing with another diacetylene, rate of cooling/recrystallization, polymerization initiators, inhibitors, additives and binder.

In another aspect of the invention there is provided a TTI made from its precursor wherein the expiration time is varied from hour to years and the activation energy from about 15 kcal/mole to about 60 kcal/mole.

In another aspect of the invention there is provided a TTI made from its precursor wherein the expiration time is varied from hour to years and the activation energy from about 15 kcal/mole to about 60 kcal/mole by varying the nature and concentration of diacetylene, co-crystallizing with another diacetylene, rate of cooling/recrystallization, polymerization initiators, inhibitors, additives and binder.

In another aspect of the invention there is provided a precursor TTI made by applying its formulation on a heat shrinkable tubing.

In another aspect of the invention there is provided a precursor TTI made by applying its formulation and a UV absorbing layer on a heat shrinkable tubing.

In another aspect of the invention there is provided a precursor TTI made by apply its formulation on a heat shrinkable tubing and a UV absorbing layer, applying tubing on a perishable container and activating by melt-recrystallization of the DA.

In another aspect of the invention there is provided a self-activating, tamper evident, heat shrinkable seal/band precursor TTI.

In another aspect of the invention there is provided a thermally-printable, self-expiring, self-activating visitor's badge made from an inactive DA layer with or without a UV absorbing.

In another aspect of the invention there is provided a thermally-printable, self-activating TTI made from an inactive DA with or without a UV absorbing layer.

In another aspect of the invention there is provided a thermally-printable, self-activating TTI made from an inactive DA which has lower radiation reactivity than that of un-melted precursor.

In another aspect of the invention there is provided a process of cooling a hot solution of a DA in a suitable solvent to crystallize the DA into an inactive phase.

In another aspect of the invention there is provided a process of cooling molten DA, with or without a binder to a temperature below its melting point, preferably at from room temperature to liquid nitrogen temperature.

In another aspect of the invention there is provided a process of cooling a hot solution of a DA in a suitable solvent and a binder to crystallize the DA into an inactive phase to make an ink of a precursor TTI.

In another aspect of the invention there is provided a process of crystallizing a diacetylene into an inactive phase from a solvent and a binder by cooling to a lower temperature, coating the formulation on a substrate and converting in to a TTI by melt recrystallization which is thermally active.

In another aspect of the invention there is provided a process of crystallizing a diacetylene into an inactive phase from a solvent and a binder by cooling to a lower temperature, coating the formulation on a substrate and converting in to a TTI by melt recrystallization which is thermally active and substantially inactive to UV light.

In another aspect of the invention there is provided a process of crystallizing a diacetylene into an inactive phase from a solvent and converting into an active phase by melt recrystallization.

In another aspect of the invention there is provided a method of controlling thermal reactivity of a precursor TTI and an active TTI made from it with or without additives, binders, crystal size and by cocrystallization with another DA.

In another aspect of the invention there is provided a method of controlling thermal reactivity of a TTI by controlling heating rate, molten time, cooling rate and cooling temperature of its precursor TTI.

In another aspect of the invention there is provided a process of activation of a precursor TTI by heating at a rate of from about 10° C./min to about 1,000° C./sec, preferably from about 10° C./sec to about 100° C./sec and a cooling rate of from about 10° C./min to about 1,000° C./sec, preferably from about 10° C./sec to about 50° C./sec.

In another aspect of the invention there is provided a process of activation of a precursor TTI wherein the time gap between melting and crystallization of a DA is between from about 0.01 sec to about 1 min, preferably from about 0.1 sec to about 2 sec.

In another aspect of the invention there is provided a process of making a precursor TTI by coating a dispersion of an inactive DA in a binder solution, with or without additives, following by drying.

In another aspect of the invention there is provided a process of making a precursor TTI by coating a dispersion of an inactive DA in a binder solution on a substrate, drying the coating and applying a layer of UV absorber and/or a non-tacky polymer which does not melt.

In another aspect of the invention there is provided a process of making a precursor TTI formulation by rapid cooling a hot solution of an inactive DA, a binder and a solvent to room temperature or to a lower temperature.

In another aspect of the invention there is provided a process of making precursor TTI formulation by rapid cooling a hot solution of an inactive DA, a binder and a solvent to an ice-water, dry ice or liquid nitrogen temperature.

In another aspect of the invention there is provided a process of shipping a precursor TTI under ambient conditions and activating before applying to a perishable.

In another aspect of the invention there is provided a process of shipping a precursor TTI under ambient conditions and activating before applying to a perishable by melting and crystallizing the precursor.

In another aspect of the invention there is provided a process of cold shipping a TTI after activating from its precursor TTI.

In another aspect of the invention there is provided a process of calibration of a melt activated TTI, such as effect on shelf life and service life under various conditions.

In another aspect of the invention there is provided a process of validation of a precursor TTI and TTI made from it.

In another aspect of the invention there is provided a process of making a stock of a precursor TTI and printing color reference bars after its calibration.

In another aspect of the invention there is provided a process of making a stock of a precursor TTI and printing color reference bars after its calibration, shipping to a user and activating before applying to a perishable.

In another aspect of the invention there is provided a process of making a thermally-printable, self-expiring, self-activating visitors' badge composed of a substrate having thereon a thermally printable coating and an inactive DA coating.

In another aspect of the invention there is provided a process of making a thermally-printable, self-expiring, self-activating visitors' badge composed of a substrate having thereon a thermally printable coating and a label of inactive DA.

In another aspect of the invention there is provided a process of making a TTI by coating an inactive TTI formulation on a heat shrinkable tubing, applying it on a perishable container and activating it by melt-recrystallization of an inactive DA.

In another aspect of the invention there is provided a process of making a self-activating, tamper evident, heat shrinkable seal/band TTI.

In another aspect of the invention there is provided an apparatus composed of at least one device for heating a precursor TTI to melt its DA and at least one cooling device for crystallization of the molten DA.

In another aspect of the invention there is provided an apparatus composed of at least one heated roller to melt the DA of a precursor TTI and at least one chilled roller or blowing cold air for rapid crystallization of the molten DA.

More particularly the invention relates to a precursor time-temperature indicating (TTI) device composed of a substrate having thereon a color changeable diacetylenic layer composed of at least one binder, particles of at least one inactive diacetylene, and optionally, one or more additives selected from a UV absorber, a melting point depressor, a nucleating agent, a release agent and opaque particles; and optionally, one or more layers selected from a UV absorbing layer, an adhesive layer, a protective layer and a release layer over the color changeable diacetylenic layer; wherein the diacetylene has low UV reactivity and either low or no thermal reactivity and has the capability of becoming thermally active with increased thermal reactivity to develop color with time and temperature upon melt recrystallization, and wherein the melt crystallized diacetylene has reduced UV reactivity.

The precursor TTI device can be opaque, translucent, semi-opaque or semi-translucent and at least one layer undergoes a visual or machine readable change including change in opaqueness, transparency, color or fluorescence when the inactive diacetylene is melted.

The binder is of the device is not substantially dissolved, swollen or plasticized during melt recrystallization of the diacetylene and can be selected from the group consisting of polybutylene, polymethylmethacrylate, polybutylmethacrylate, polybutylmethacrylate/isobutylmethacrylate, polyethylene, poly(ethylene-co-acrylic acid), poly(ethylmethacrylate), polyethylene/vinylacetate, poly(isobutylmethacrylate), polyvinylbutyral, polyvinylchloride, polyvinylstearate, poly(ethylene-co-acrylic acid), poly(ethylene-co-methacrylic acid), polybutadiene, polyvinylacetate, poly(ethylene-co-butylacrylate-co-carbon monoxide), poly(o-cresyl glycidyl ether)-formaldehyde, poly(ethyelene-co-1-butene), poly(ethylene-co-methyl acrylate), polyethylene-co-vinylacetate-co-carbon monoxide), polyhexamethyleneadipate and polyhexamethylenevinylene.

In an aspect of the invention the binder is a UV cured polymer.

In another aspect of the invention the precursor device has at least one color reference bar for monitoring expiration of a perishable by matching its color with the color of the color changeable layer when the diacetylene is melt recrystallized.

The release layer of the precursor device is composed of the group consisting of one or more materials selected from polysiloxane, a silane, a polysilicone, a fluorosilicone, polyvinyl alcohol and polytetrafluoroethylene. The release layer is preferably non-tacky at the melting temperatures of the diacetylene.

The melting point depressor of the precursor device is able to lower the melting point of the diacetylene. In one aspect of the invention the melting point depressor is a low melting solid.

The nucleating agent of the precursor device is preferably a nano- or micron-sized particles of an organic or inorganic material. A non-limiting example is a nano- or micron-sized particles of silver halide.

One or more of the inactive diacetylenes of the invention can be selected from the group consisting of R—C≡C—C≡C—R, where R is selected from: $(CH_2)_b$—H; $(CH_2)_b$—OH; $(CH_2)_b$—OCONH—R1; $(CH_2)_b$—O—CO—R1; $(CH_2)_b$—O—R1; $(CH_2)_b$—COOH; $(CH_2)_b$—COOM; $(CH_2)_b$—NH_2$; $(CH_2)_b$—CONHR1; $(CH_2)_b$—NHCONHR1; $(CH_2)_b$—CO—O—R1; where b=1-10, preferably 1-4, and R1 is substituted or unsubstituted alkyl or phenyl where the substituent group is a alkyl or phenyl group, with or without one or more substituents selected from the group of —Cl, —Br, —I, F, —NO_2, alkyl, phenyl, alkoxy and phenoxy; and M is a cation, such as Na$^+$ or (R1)$_3$N$^+$; and their cocrystallized mixtures.

In a particular aspect of the invention the inactive diacetylene is a cocrystallized mixture of diacetylenes or a mixture of more than one diacetylene.

The particles of the inactive diacetylene or co crystallized mixture can be obtained by milling the diacetylene or by rapid cooling of the diacetylene from its solution.

Examples of the diacetylene are selected from: R—C≡C—C≡C—R, where R is selected from: (CH$_2$)$_b$—H; (CH$_2$)$_b$—OH; (CH$_2$)$_b$—OCONH—R1; (CH$_2$)$_b$—O—CO—R1; (CH$_2$)$_b$—O—R1; (CH$_2$)$_b$—COOH; (CH$_2$)$_b$—COOM; (CH$_2$)$_b$—NH$_2$; (CH$_2$)$_b$—CONHR1; (CH$_2$)$_b$—NHCONHR1; (CH$_2$)$_b$—CO—O—R1; where b=1-10, preferably 1-4, and R1 is substituted or unsubstituted alkyl or phenyl, where the substituent group is a alkyl or phenyl group, with or without one or more substituents selected from the group of —Cl, —Br, —I, F, —NO$_2$, alkyl, phenyl, alkoxy and phenoxy; and M is a cation, such as Na$^+$ or (R1)$_3$N$^+$; and their cocrystallized mixtures, more specifically diacetylenes, R—C≡C—C≡C—R, where R=(CH$_2$)$_3$—O—CO—(CH$_2$)$_{14}$CH$_3$, (CH$_2$)$_3$—O—CO—NH-m-chlorophenyl, (CH$_2$)$_2$—O—CO—NH-m-chlorophenyl, CH$_2$—O—CO—NH-m-chlorophenyl, CH$_2$—O—CO—NH-m-tolyl, CH$_2$—O—CO—NH-o-chloropheny, CH$_2$—O—CO—NH-o-methoxypheny, CH$_2$—O—CO—NH-p-chloropheny, and CH$_2$—O—CO—NH-phenyl.

In another aspect of the invention, the precursor device has a shelf life of a week to a decade at room temperature without development of any noticeable change including change in color.

In another aspect of the invention the opaque particles of the precursor device are nano- to micron-sized organic or inorganic materials, such as cellulose, zinc oxide, alumina, titanium dioxide and/or silicone dioxide.

In another aspect of the invention the precursor device is activated by rapid heating to melt the diacetylene followed by a rapid cooling to crystallize the molten diacetylene, more particularly by heating the diacetylenic layer from room temperature to above the melting point of the diacetylene in seconds or less and cooled to room temperature from the molten state in seconds or less by passing over at least one heated device, such as a heated roller or blowing hot air and crystallized from the molten diacetylene by passing over a cooling device, such as a cooled roller or blowing cold air. Even more particularly, the diacetylene is melted with an infrared light from a IR lamp, IR laser, IR LED, or induction heating or a combination thereof.

In another aspect of the invention the substrate of the precursor device is a heat shrinkable plastic tubing.

In another aspect of the invention, the precursor device can be activated by melting the diacetylene with a thermal printer.

In another aspect of the invention a composition for making a precursor TTI device comprises at least one binder, particles of at least one inactive diacetylene, an organic solvent or water and optionally, one or more additives selected from the group of a UV absorber, a melting point depressor, a nucleating agent, a release agent and opaque particles; wherein the diacetylene has low UV reactivity and either low or no thermal reactivity. The composition can be made by heating the composition to dissolve the diacetylene and cooling to a lower temperature to crystallize the diacetylene. This composition can be made by milling the particles of diacetylene with or without one or more of additives selected from a binder, UV absorber, a melting point depressor and a nucleating agent.

Another aspect of the invention relates to an apparatus for the melt activation of the precursor device composed of at least one heating device to melt the diacetylene and at least one cooling device to cause crystallization of the molten diacetylene. More particularly, in one aspect of the apparatus the heating device is a heated roller and the cooling device is a chilled roller.

Yet another aspect of the invention relates to a TTI device comprising a substrate having thereon: a color changing layer composed of at least one binder, particles of at least one melt recrystallized diacetylene, and optionally, one or more additives selected from a UV absorber, a melting point depressor, a nucleating agent, a release agent and opaque particles; and optionally, one or more layers selected from a UV absorbing layer, an adhesive layer, a protective layer and a release layer over the color changing layer; and at least one color reference bar for monitoring expiration of a perishable by matching its color with the color changing layer wherein the diacetylene develops color with time and temperature; and wherein the diacetylene has low UV reactivity.

The binder of the TTI device is selected from the group consisting of a polyacrylic, polybutylene, polymethylmethacrylate, polybutylmethacrylate, polybutylmethacrylate/isobutylmethacrylate, polyethylene, poly(ethylene-co-acrylic acid), poly(ethylmethacrylate), polyethylene/vinylacetate, poly(isobutylmethacrylate), polyvinylbutyral, polyvinylchloride, polyvinylstearate, poly(ethylene-co-acrylic acid), poly(ethylene-co-methacrylic acid), polybutadiene, polyvinylacetate, poly(ethylene-co-butylacrylate-co-carbon monoxide), poly(o-cresyl glycidyl ether)-formaldehyde, poly(ethyelene-co-1-butene), poly(ethylene-co-methyl acrylate), polyethylene-co-vinylacetate-co-carbon monoxide), polyhexamethyleneadipate and polyhexamethylenevinylene.

The release layer of the TTI device is composed of one or more materials selected from polysiloxane, a silane, a polysilicone, a fluorosilicone, polyvinyl alcohol and polytetrafluoroethylene.

One or more diacetylenes of the TTI device are selected from the group consisting of R—C≡C—C≡C—R, where R is selected from: (CH$_2$)$_b$—H; (CH$_2$)$_b$—OH; (CH$_2$)$_b$—OCONH—R1; (CH$_2$)$_b$—O—CO—R1; (CH$_2$)$_b$—O—R1; (CH$_2$)$_b$—COOH; (CH$_2$)$_b$—COOM; (CH$_2$)$_b$—NH$_2$; (CH$_2$)$_b$—CONHR1; (CH$_2$)$_b$—NHCONHR1; (CH$_2$)$_b$—CO—O—R1; where b=1-10, preferably 1-4, and R1 is substituted or unsubstituted alkyl or phenyl, where the substituent group is a alkyl or phenyl group, with or without one or more substituents selected from the group of —Cl, —Br, —I, F, —NO$_2$, alkyl, phenyl, alkoxy and phenoxy; and M is a cation, such as Na$^+$ or (R1)$_3$N$^+$; and their cocrystallized mixtures.

The rates of color development and activation energy of the TTI device are varied by varying the nature and concentration of diacetylene, co-crystallization with another diacetylene, rate of cooling or recrystallization of the molten diacetylenes, polymerization initiators, inhibitors, additives and a binder.

The expiration time of the TTI device is varied from hour to years and the activation energy from 15 kcal/mole to 60 kcal/mole.

In another aspect of the invention the substrate of the TTI device is a heat shrunken tubing Yet another aspect of the invention relates to a process of making a TTI device which process comprises heating the precursor TTI device described above to a temperature above the melting point of the inactive diacetylene; and cooling the heated precursor TTI device to below the melting point of the diacetylene to obtain a melt recrystallized diacetylene. More particularly, the device can be heated to about 10° C. to 30° C. above the melting point of the inactive diacetylene. The heated device can then be cooled to room temperature or below.

Yet another aspect of the invention relates to a process of making the composition useful to making the precursor device which comprises dissolving a diacetylene in an organic solvent or water with heating; cooling the hot solution to crystallize the diacetylene into an inactive phase. More particularly, the solution of a diacetylene can be cooled to room, ice-water, dry ice or liquid nitrogen temperature.

Yet another aspect of the invention relates to a process of making the precursor device of by applying on a substrate a composition comprising at least one binder, particles of at least one inactive diacetylene, an organic solvent or water and optionally, one or more additives selected from the group of a UV absorber, a melting point depressor, a nucleating agent, a release agent and opaque particles; wherein the diacetylene has low UV reactivity and either low or no thermal reactivity. More particularly the process optionally applying additional one or more layers selected from a UV absorbing layer, an adhesive layer, a protective layer and a release layer over the color changeable layer.

Another aspect of the invention relates to a process of activation of the precursor device comprising melting the device above the melting point of the diacetylene and then cooling the device below the melting point of the diacetylene.

Yet another aspect of the invention relates to a method of controlling the thermal reactivity of the TTI device by controlling a heating rate, a molten time, a cooling rate and a cooling temperature. More particularly the heating rate can be controlled to a range of between about 10° C./min and about 200° C./sec and the cooling rate to a range of between about 10° C./min and about 200° C./sec, even more particularly controlling the heating range between about 10° C./sec and about 50° C./sec and the cooling rate is from about 10° C./sec to about 50° C./sec.

The time gap between melting and crystallization of the diacetylene can be controlled from about 0.01 sec to about 1 min more particularly from about 0.1 sec to about 2 sec.

Yet another aspect of the invention relates to a precursor device which is activated by a thermal printer to make a time temperature indicator or a visitor's badge.

Another aspect of the invention relates to a process of making a visitor's badge composed of a substrate having thereon a thermally printable layer and a layer of the composition used to make the precursor device of the invention.

Another aspect of the invention relates to a process of making a time-temperature indicating device by coating the composition used to make the precursor device on a heat shrinkable tubing. The time-temperature device can be activated by applying the device on a perishable container and activating it by heat wherein the tube shrinks and the diacetylene melts and crystallizes upon cooling.

Another aspect of the invention relates to a method of activation of the precursor device to make a TTI device comprising melting the diacetylene of the precursor device with a heating device and crystallizing the diacetylene with a cooling device. More particularly, the heating can be done with a heated roller and cooling can be done with cooling roller.

In one aspect of the invention the UV absorber of precursor device can be a benzophenone, a benzotriazole, a benzoate, an oxanilide or a salicylate.

In another aspect of the invention the substrate of the precursor device can be paper, polyethylene, polypropylene, polyester, cellulose acetate, or polyvinyl chloride and their copolymers.

Yet another aspect of the invention relates to a precursor TTI toner composition comprising at least one inactive diacetylene and at least one binder. More particularly, the toner composition can comprise from about 50 to about 95 weight percent of the binder, about 2 to about 50 weight percent of the inactive diacetylene, about 0 to about 6 weight percent of a wax, about 0 to about 3 weight percent charge control agent, about 0.25 to about 1 weight percent flow agent and 0 to about 1 weight percent other additives. A TTI toner device made from the precursor TTI toner composition by melting and cooling a layer of precursor composition a substrate. The melting and cooling of the precursor composition can be accomplished with a laser printer.

BRIEF DESCRIPTION OF THE FIGURES

The foregoing and other objects, features and advantages will be apparent from the following description of the preferred embodiments of the invention as illustrated in the accompanying drawings, examples and preferred embodiment. The invention is more fully described below in conjunction with the figures wherein.

DETAILED DESCRIPTION OF THE INVENTION

Figure 1:
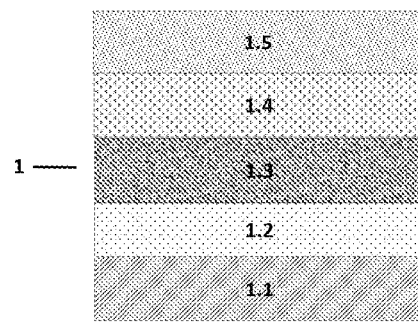
FIG. 1 shows a cross sectional view of different layers of a TTI device and its precursor.

In order to explain the invention more clearly the following definitions are presented.

Activation: a process of converting a substantially inactive diacetylene into a substantially active/polymerizable form, usually thermally polymerizable.

Active diacetylene: A diacetylene which develops color by the solid state polymerization upon thermal annealing and/or exposure to ionizing radiation, such as UV light and X-ray.

Active phase: A crystallographic phase/structure/modification of a diacetylene which polymerizes either upon thermal annealing or exposure to ionizing radiation.

Active TTI or TTI: A time-temperature indicator which is capable of monitoring integral value of time and temperature.

DA: A diacetylene (R—C≡C—C≡C—R, where R is a substituent group).

DA-TTI: An active or inactive TTI composed of at least one diacetylene.

Inact DA: A substantially inactive diacetylene.

Inact toner: A toner composed of at least one inactive diacetylene.

Inactive diacetylene: A crystallographic form/phase/modification of a diacetylene which shows none, negligible or acceptably low polymerization upon heat annealing and/or exposure to ionization radiation. A diacetylene is considered inactive when it does not readily develop noticeable color, for example, in about a month at room temperature. The term "inactive", "inact" and "low thermal reactive" are used interchangeably herein.

Inactive: Substantially un-polymerizable, usually a diacetylene.

Melt-recrystallization, melt-crystallization or melt-activation: A process of heating a solid diacetylene to melt followed by cooling it below its melting point, usually at room temperature or below a temperature where it becomes solid (e.g., a thermally inactive diacetylene become thermally active upon melting and cooling to room temperature). The terms melt-recrystallization, melt-crystallization or melt-activation are used interchangeably.

Phase change: A change in crystal structure or molecular packing of a diacetylene. A phase change herein usually refers to a change from a substantially low thermal reactivity (inactive) to a substantially higher thermal reactivity (active) form. The phase change can be from substantially active to substantially inactive form.

Phase or form: When it refers to a diacetylene, a form or a phase means a crystal structure of a diacetylene in which the molecules are packed in a particular manner.

Precursor TTI: A TTI device composed typically of at least one inactive diacetylene. Precursor TTI are not limited to diacetylenes only. Any composition or a mixture of compositions, which are thermally inactive and become thermally active and develops noticeable or recordable change can also be used as a precursor TTI. An un-activated TTI is also refer to as a precursor TTI or TTI precursor.

Radiation reactivity: Polymerizability of a diacetylene with radiation, such as UV, electrons, neutrons, protons and gamma/X-ray.

Reactivity: Usually refers to polymerizability of a diacetylene, e.g., upon thermal annealing or radiation.

Thermal reactivity: Polymerizability of a diacetylene upon thermal annealing.

Time-temperature indicator or TTI: A device which monitors integral value of time and temperature.

UV layer: A layer of coating which has ability to absorb ultra violet (UV) light of about 400 nm to about 100 nm. The UV layer may be a UV absorbing polymer or a polymer containing one or more UV absorbers.

The indicating system of the present invention can best be more fully described by reference to the figures. For simplicity and clarity of illustration, figures are not necessarily drawn to scale.

A cross sectional view of a TTI device of the present invention is shown in FIG. 1. The basic device 1 is composed of a reactive layer 1.3 which is composed of fine particles of a diacetylene or cocrystallized diacetylenes dispersed in a polymeric binder and optionally one or more additives, such as melting point depressor, UV absorber, reaction initiator or inhibitor and surfactant coated on a substrate, such as paper or plastic film 1.1 which may have a primer layer 1.2. The reactive layer 1.3 may have a UV absorbing layer 1.4 which can be composed of a UV absorber in a polymeric binder to protect diacetylenes from UV light and/or a non-tacky or non-melting release layer 1.5. The diacetylene in the precursor TTI will be inactive. The diacetylene in layer 1.3 will become active and polymerizable upon melt recrystallization, i.e., upon heating and cooling the device. The device may have additional layers, e.g., a laminated film as needed.

Figure 2:
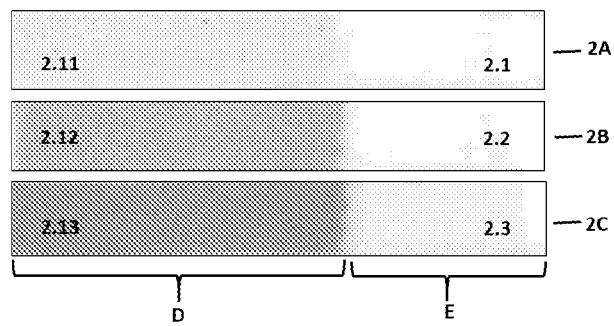
FIG. 2 shows un-activated and melt activated TTI samples made from an inactive diacetylene annealed at 80° C. for different periods of time.

FIG. 2 shows strips 2A, 2B and 2C of a TTI device of the current invention made from a diacetylene 2PmCl (R—C≡C—C≡C—R, where R=(CH$_2$)$_2$—O—CO—NH-m-chlorophenyl) in a polymeric binder and annealed for different periods of time at 80° C., before E, after melt-activating a portion D by heating at 150° C. for about a second. As-coated strip (precursor TTI, not shown) was translucent white as shown in portion 2.1. One end 2.1 of the strip (precursor TTI) was not melted while the other end 2.11 of the strip was melt-activated. FIG. 2A shows the strip before annealing. FIGS. 2B and 2C show the color (purple-blue) development of the strip 2A after annealing for 2 hours and 16 hours respectively at 80° C. The melt-activated portion 2.11 developed color and the color intensified with time and temperature of annealing as shown in portions 2.12 and 2.13, while the un-activated portion 2.1 either did not develop color or developed negligible color as shown in portions 2.2 and 2.3. As can be seen from FIG. 2, un-activated TTI, E either does not develop or develop negligible color upon thermal annealing while the melt-activated TTI, D develops color rapidly and the color intensifies with time and temperature of annealing. The rate of color development can be varied by cocrystallization with other diacetylenes and also by varying the nature of the binder and an additive. The un-melted samples which were stored at room temperature for six months did not develop any noticeable color while the melt-activated samples were purple. The results clearly indicate that a precursor TTI can be stored for months and probably years at room temperature.

Figure 3:
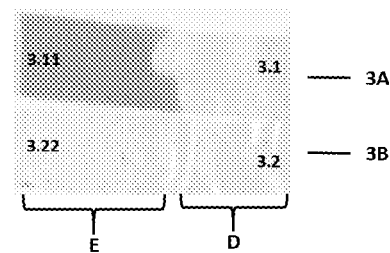
FIG. 3 shows an activated and an un-activated TTI with and without a UV absorbing layer exposure to UV light.

FIG. 3 shows two strips of a TTI device of the current invention made from a diacetylene 2PmCl (R—C≡C—C≡C—R, where R=(CH$_2$)$_2$—O—CO—NH-m-chlorophenyl) before E and after D melting. The strip 3A was not coated with a UV absorber in a binder while the strip 3B was coated with a UV absorbing layer. Portions 3.11 and 3.22 of the strips were not melt activated while portions 3.1 and 3.2 were melt activated by heating at 150° C. for about a second. The strips were exposed to 254 nm UV light from a 40-watt UV lamp (Ushino G1578, Japan) at 30 cm for one hour. Commercially available TTI samples made from a diacetylene (VVM2, VVM7, VVM14 and VVM30 of Temptime Corporation, Morris Plains, NJ) developed dark blue-purple color within a minute (indicating expiration). The un-melted portion 3.11 of the precursor TTI without a UV protection is slight sensitive to UV light and hence developed color upon prolonged exposure to intense UV light. However, the melted portion and UV coated portion 3.22 is highly insensitive to prolonged exposure to intense UV light. The melt activated portions 3.1 and 3.2 are extremely insensitive to prolonged exposure to intense UV light whether they are protected with a UV absorbing layer or not. We also observed that UV sensitivity is significantly reduced by applying a non-UV absorbing polymer layer on precursor TTI.

Figure 4:
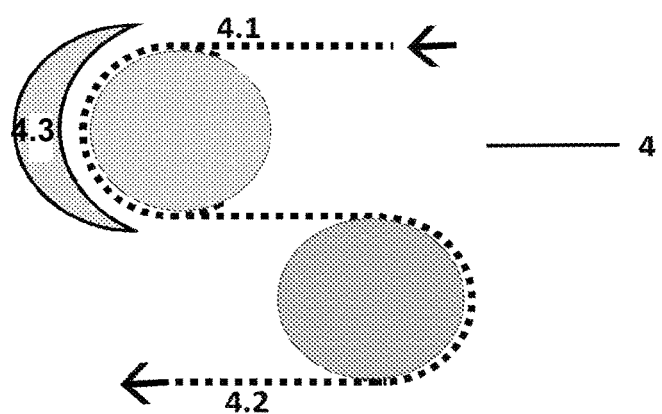
FIG. 4 shows a schematic presentation of some key components of an apparatus for heating a precursor TTI and cooling it to make an active TTI.

FIG. 4 shows a schematic presentation of key components of a production apparatus for melt activation of a roll having a large number labels of a precursor TTI. A basic production apparatus 4 for melt activation can be composed of a system for rapid heating of a precursor TTI and rapid cooling of melt-activated TTI, a system for unwinding of precursor TTI roll (not shown) and a system for winding the melt-activated roll (not shown). The melting of precursor TTI 4.1 can be done by many different ways, such as by passing over a heated roller 4.4 or by passing between two heated rollers. The melting of inactive TTI can also be done by other methods, such as heating with IR light from a IR lamp or a laser light 4.3. The cooling of the melt activated TTI for re-crystallization of molten diacetylene can be done by many ways, such as passing over or between chilled rollers 4.5 or by blowing cold air. A roll of precursor TTI 4.1 will pass over a hot roller 4.4 to melt the inactive diacetylene followed by passing over a cold roller 4.5 to crystallize the molten diacetylene into an active phase. The surface of rollers 4.4 and 4.5, preferably should be non-sticky, non-tacky, and releasing. The rollers may have a Teflon (polytetrafluoroethylene) or polysilicone coating. The melt-activated TTI 4.2 will develop color with time and temperature.

Figure 5:
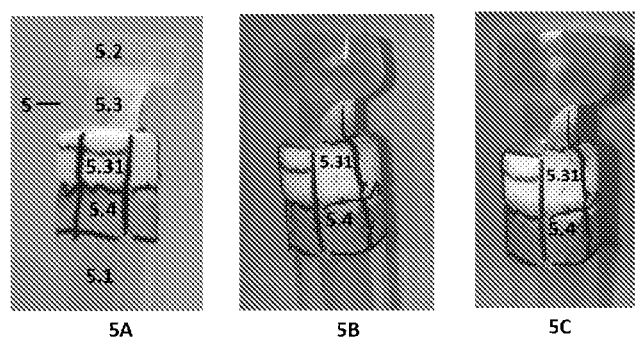
FIG. 5 shows a tamper evident, heat shrunk TTI seal on a vial annealed at 70° C. for different periods of time.

A self-activating, tamper evident, heat shrinkable seal/band TTI is shown in FIG. 5. A heat shrinkable tubing 5 was partially coated with a dispersion of a diacetylene 2PmCl (R—C≡C—C≡C—R, where R=$(CH_2)_2$—O—CO—NH-m-chlorophenyl) 5.31 and 5.4. The coated tubing was held over a vial 5.1 and heat shrunk with a hot air blower. The melting point 2PmCl was higher than that of the heat shrinkable tube and hence the bottom portion of the tubing 5.4 was heated further till the coating melted as shown in FIG. 5A. The top portion 5.2 of the tubing was not heated to melt, while the portions 5.3 and 5.31 were heated to melt the tubing but not enough to melt the diacetylene. The portion 5.3 shrunk completely. The vial assembly was placed in an oven at 70° C. for a different period of time, e.g., FIG. 5B for 1 hour and FIG. 5C for 16 hours. As can be seen from FIGS. 5B and 5C, the coating 5.31 did not develop color upon annealing as the diacetylene was not melted while coating 5.4 developed purple-blue color and color intensified with time and temperature because it was heated sufficiently to melt-crystallize the diacetylene into an active phase.

Figure 6:
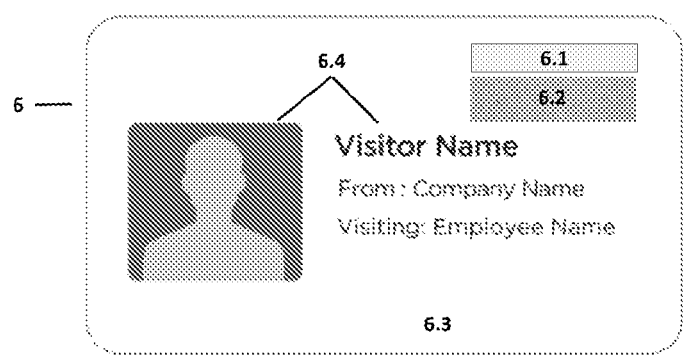
FIG. 6 shows a schematic presentation of a top view of a thermally-printable, self-expiring, self-activating visitors' badge having a coating on an inactive DA.

FIG. 6 shows a schematic presentation of a thermally-printable, self-activating and self-expiring visitors' badge. The badge 6 can be composed of a substrate, such as paper or plastic film having a layer of thermally printable composition (known in the art) 6.3 except for a small area for coating of a precursor TTI composition 6.1 and optionally a color reference bar 6.2. Using a thermal printer and a software, one can print information 6.4 in black and white on the thermal coating 6.3 and activate the inactive DA coating 6.1 simultaneously. The melt-activated DA coating 6.1 will develop color with time under ambient conditions. If a color reference bar 6.2 is printed adjacent to inactive DA coating, it will indicate expiration of the badge, i.e., when the melt-activated DA coating 6.1 is matching or darker than the color reference bar 6.2. As the sensor 6.1 develops color with time and temperature, the device of FIG. 6 can be used a TTI as well. The information printed will be that of a perishable. Thus, a thermal printer can be used to activate a precursor TTI to make a TTI.

As an alternative to a design shown in FIG. 6, a thermally-printable, self-activating and self-expiring visitors' badge 7 can be created by applying a thin white opaque sticker of a precursor TTI 7.1. The badge 7 can be composed of a substrate, such as paper or plastic film having a layer of thermally printable composition 7.3. An opaque precursor TTI sticker 7.1 having an adhesive, e.g., pressure sensitive adhesive (PSA) is applied, e.g., at one corner on the badge 7. The precursor TTI sticker 7.1 can be composed of a thin opaque white substrate having a PSA layer on one side and a precursor TTI coating 7.11 and optionally a color reference bar 7.12 adjacent to 7.11 to indicate expiration. Using a thermal printer and a software, one can print information 7.4 in black and white on the thermal coating 7.3 and simultaneously activate the inactive DA of coating 7.11. The melt activated DA will slowly develop color with time. If a color reference bar 7.12 is printed adjacent to the DA coating, it will indicate when the badge expired, i.e., when the melt-activated DA coating is matching or darker than the color reference bar. As the sensor 7.11 develops color with time and temperature, the device of FIG. 7 can be used a TTI as well. The information printed will be that of a perishable.

Figure 7:
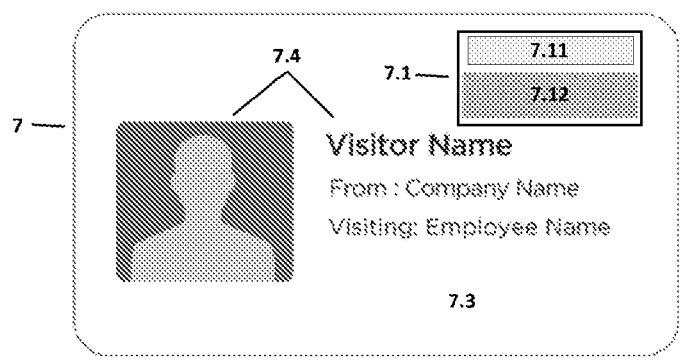
FIG. 7 shows a schematic presentation of a top view of a sticker of a thermally-printable, self-expiring, self-activating visitors' badge.
Figure 8:
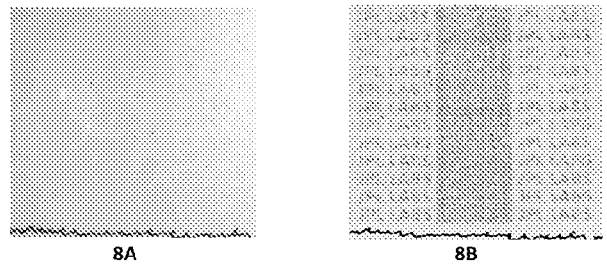
FIG. 8 shows an example of a TTI and a visitor's badge made from an inactive DA, activated by a thermal printer before (A) and after (B) annealing at 40° C. for 3 days.

FIG. 8 is a demonstration of the concepts disclosed in FIGS. 6 and 7. Portions of a coating of inactive 3E16 ((R—C≡C—C≡C—R, where R=$(CH_2)_3$—O—CO—$(CH_2)_{14}CH_3$) on a film was selectively melt activated with a thermal printer. The bar and labels were barely noticeable as shown in FIG. 8A. The area melted by the thermal printer developed red color and red color darkened with time and temperature as shown in FIG. 8B. The area not melted did not develop color. The results of FIG. 8 show that a TTI and a visitor badge can be created by selective activation of a coating of an inactive DA on a substrate by selective heating with device like thermal printer or a laser.

The TTI devices by melt recrystallization of inactive diacetylenes reported in the literature do not provide reproducible and consistent results and lack many features. The known art TTI devices lack many materials and processes to make a field usable TTI.

Diacetylenes:

A preferred class of the indicator material for the TTI is diacetylenes having general formula, R'—C≡C—C≡C—R", where R' and R" are the same or different substituent groups. Though this class of diacetylenes is preferred, other diacetylenes having the following general formulas can also be used: higher acetylenes: R'—$(C≡C)_n$—R", where n=3-5; split di and higher acetylenes: R'—$(C≡C)_m$—Z—$(C≡C)_o$—R", where Z is any diradical, such as —$(CH_2)_n$— and —$C_6H_4$—, and m and o is 2 or higher; and polymeric di and higher acetylenes: [-A-$(C≡C)_n$-B-]$_x$, where A and B can be the same or different diradical, such as —$(CH_2)_b$—, —OCONH—$(CH_2)_b$—NHCOO—, and —OCO$(CH_2)_b$—OCO—, where R' and R" can be the same or different groups.

The preferred diacetylenes include those where R' and R" are selected from: $(CH_2)_b$—H; $(CH_2)_b$—OH; $(CH_2)_b$—OCONH—R1; $(CH_2)_b$—O—CO—R1; $(CH_2)_b$—CO—O—R1; $(CH_2)_b$—O—R1; $(CH_2)_b$—COOH; $(CH_2)_b$—COOM; $(CH_2)_b$—NH$_2$; $(CH_2)_b$—CONHR1; $(CH_2)_b$—NHCONHR1; where b=1-20, preferably 1-4, and R1 is substituted or unsubstituted alkyl or phenyl, and M is a cation, such as Na$^+$ or $(R1)_3N^+$ and their cocrystallized mixtures. The substituent groups of R1 can be alkyl or phenyl, for example, including one or more of —Cl, —Br, —I, F, —NO$_2$, alkyl, phenyl, alkoxy and phenoxy.

The preferred diacetylenes are the derivatives of 2,4-hexadiyne, 2,4-hexadiyn-1,6-diol, 3,5-octadiyn-1,8-diol, 4,6-decadiyn-1,10-diol, 5,7-dodecadiyn-1,12-diol and diacetylenic fatty acids, such as tricosa-10,12-diynoic acid (TC), pentacosa-10,12-diynoic acid (PC), their esters and amides, organic and inorganic salts and cocrystallized mixtures thereof. The most preferred derivatives of the diacetylenes are urea or urethane derivatives of 2,4-hexadiyn and their cocrystallized mixtures.

Further preferred diacetylenes are those having urethane and urea derivatives, substituted or unsubstituted alkyl, aryl, benzyl, methoxy phenyl, alkyl acetoacetate, fluoro phenyl, alkyl phenyl, halo-phenyl, cyclohexyl, tolyl and ethoxy phenyl of 2,4-hexadiyn, 3,5-octadiyn, 4,6-decadiyn and 5,7-dodecadiyn. The prefer urethane and urea derivatives are substituted or unsubstituted methyl, ethyl, propyl, butyl and phenyl derivatives of 2,4-hexadiyn, 3,5-octadiyn, 4,6-decadiyn and 5,7-dodecadiyn and their cocrystallized mixtures.

The following are some of the preferred derivatives of 2,4-hexadiyn-1,6-diol: urethane (—OCONH) derivatives, $R'CH_2$—C≡C—C≡C—$CH_2R'$, including: hexyl urethane: $R'$=—$OCONH(CH_2)_5CH_3$; pentyl urethane: $R'$=—$OCONH(CH_2)_4CH_3$; butyl urethane: $R'$=—$OCONH(CH_2)_3CH_3$; ethyl urethane: $R'$=—$OCONHCH_2CH_3$; methyl urethane: $R'$=—$OCONHCH_3$; ester (—OCO—) derivatives, $R'''CH_2$—C≡C—C≡C—$CH_2R'''$, including: butyl ester: $R'''$=—$OCO(CH_2)_3CH_3$; ethyl ester: $R'''$=—$OCOCH_2CH_3$; methyl ester: $R'''$=—$OCOCH_3$; asymmetrical diacetylenes including: $R'$—C≡C—C≡C—$R''$, where for example, $R'$=—$CH_2OCONH(CH_2)_5CH_3$ and $R''$=—$CH_2OCONH(CH_2)_4CH_3$; and their cocrystallized mixtures. The further preferred diacetylenes are derivatives of 3,5-octadiyn-1,8-urethane, 4,6-decadiyn-1,10-urethane and 5,7-dodecadiyn-1,12-urethane, e.g., hexyl urethane: $R'$=—$OCONH(CH_2)_5CH_3$; pentyl urethane: $R'$=—$OCONH(CH_2)_4CH_3$; butyl urethane: $R'$=—$OCONH(CH_2)_3CH_3$; propyl urethane: $R'$=—$OCONH(CH_2)_2CH_3$; ethyl urethane: $R'$=—$OCONHCH_2CH_3$; methyl urethane: $R'$=—$OCONHCH_3$ and their cocrystallized mixtures.

The further preferred diacetylenes salts of mono of di-substituted (symmetrical or asymmetrical) diacetylene having carboxylic acid (—COOH) functionality. The carboxylic acid functionality can be fully or partially neutralized with a base. The examples of diacetylene having acid functionality are MOOC—$(CH_2)_n$—C≡C—C≡C—$(CH_2)_m$—COOM or $H_3C$—$(CH_2)_n$—C≡C—C≡C—$(CH_2)_m$—COOM where M is a cation, such as $Na^+$, $K^+$, $Li^+$, $Ca^{++}$ or $(R1)_3N^+$.

Further preferred DA are those having halo substitution and long chain as a part of the substituent group, e.g., phenyl substituted with —F, —Cl, —Br, I, and —O-alkyl.

Diacetylenes having mono, di, tri, tetra or penta substituted phenyl group can be used for precursor TTI. The substituent group can be alkyl, phenyl, halo, alkoxy and phenoxy.

Further preferred are the diacetylenes listed in Table 1 and those used in the Examples.

Further preferred are the diacetylenes which have a long induction period of polymerization.

Some active diacetylenes can be made inactive by adding selecting proper additives, binders and method of crystallization, and by cocrystallization with another suitable diacetylene. Some active diacetylenes can also be made inactive by melt recrystallization. To use a diacetylene for monitoring radiation, one need to reduce the thermal reactivity which can be achieved by making the diacetylene thermally inactive by melt crystallization.

DA undergoing a phase change from inactive to an active phase in the solid state without melting during heating can also be used as activated TTI.

Diacetylene can be made inactive by forming a solid solution with a binder or an additive and made active upon melting.

Acid-Amine Mixtures:

DA acids (such as tricosadiynoic acid and pentacosadiynoic acid) neutralized with an inorganic base, such as sodium bicarbonate and organic base, such as an alkyl or aromatic amine can also be used for the TTI system. Similarly, DA amines neutralized with an inorganic acid, such as hydrochloric acid and organic acid, such as an alkyl or aromatic acid can also be used for the system. An amine can be alkyl or aryl and can be primary, secondary or tertiary. An acid can be carboxylic acid or a mineral acid, such as hydrochloric or phosphoric acid.

DA with Increase in Thermal Reactivity:

A DA for the precursor TTI system does not need to be 100% thermally inactive. DA with acceptably low thermal reactivity can be used as a precursor TTI, for example by storing at lower temperature, e.g., in a refrigerator or freezer till need to be activated by melt recrystallization into higher reactivity form.

Precursor TTI Related Properties of DA:

A unique property of diacetylenes is that some of them can be crystallized into an inactive phase (no substantial color development) from a solution and made active (means polymerizable with time and temperature or radiation) if crystallized from melt (melted and cooled). For polymerization to occur, the packing of molecules, i.e., the distance and angle between the molecules in the crystal must be proper (e.g., identity period of ~4.9 Angstroms and an inclination angle of ~45'). A small number of diacetylenes crystallize into an inactive phase from solvents and crystallize into an active phase when crystallized from melt (melted and cooled). This technique/principle of crystallization of a diacetylene into an inactive (un-polymerizable) phase from solution so the TTI made from it can be stored for a very long time and crystallization into an active (polymerizable) phase by melt crystallization before applying on a perishable container is used to make precursor TTI.

Making of Precursor TTI:

The following are some of the major key steps of making a precursor TTI:

Prepare the ink by one pot method, i.e., synthesize the DA by selecting right reactants and ingredient in proper proportions and when the reaction is complete, add binder and additives. Heat the solution to dissolve the diacetylene, if required.

If the diacetylene already synthesized, dissolve it in a hot solution of a binder with or without the additives as required.

Pass the above solutions/inks through a cooling coil, e.g., maintained at about 4° C. (ice water) or a lower temperature, collect the solution in form of crystalline dispersion of the diacetylene. The solution can be poured into liquid nitrogen or over dry ice to make finer crystals of the diacetylene.

Wait, if require, at the low temperature for complete crystallization of diacetylene.

Bring the mixture to room temperature and homogenize and adjust the viscosity of the inactive ink.

Making of Precursor TTI:

The inactive ink prepared by the above or any other method, such as by dispersing fine particles of inactive DA in a binder solution, can be coated on a substrate, such as a paper and plastic film. The substrate may have a prime coat or sub-coat. The coated substrate is dried in an oven by blowing hot air. The temperature of the hot air need to be controlled to prevent overheating. A UV absorbing (a UV absorber in a polymeric binder) and/or a non-tacky/non-meltable layer (e.g., that of silicone or Teflon) is applied over the inactive DA layer as a top layer. The objective of the UV absorbing layer is to protect the inactive DA from polymerization in case if it is sensitive to UV light. The objective of the non-tacky or non-melting release layer is to prevent the coatings from sticking to the heated rollers when precursor TTI is melt activated.

Activation of Precursor TTI:

The inactive DA layer (often refer to as a reactive layer) does not develop color with time and temperature under normal storage and ambient conditions. The precursor TTI need to be activated by melting the inactive DA and crystallizing into an active phase which polymerizes with time and temperature. The rate and temperature of heating need to be controlled. A rapid melting will be preferred to prevent degradation (if any) and molten DA dissolving the binder. The rate of cooling also need to be controlled. A rapid cooling will be required for small crystal formation and for rapid activation. The technology for rapid melting and cooling of precursor TTI exist but the equipment need to be modified. FIG. 4 is a schematic presentation of melting and cooling apparatus for activation of a precursor TTI. The heating can be done with a conventional electric heater, steam, hot air, IR lamp/LED and IR laser. Cooling can be done by blowing cold air or circulating cold water though the roller. If heated with an IR lamp, the TTI should preferably be outside so it can be directly heated by the IR lamp. If heated with a heated roller, the TTI should preferably be inside so it can have a direct contact with the roller.

Addition of Heat Stabilizer/Shelf Life Extenders:

Heat stabilizers or shelf life extenders disclosed in U.S. Pat. No. 7,476,874 can be used to reduce the thermal reactivity and increase the shelf life of precursor TTI. The disclosures in U.S. Pat. No. 7,476,874 are hereby incorporated in their entirety by reference. Thus, a DA having slight thermal reactivity which makes a DA not usable as TTI can be made suitable for precursor TTI by adding an additive, a heat stabilizer.

Reducing UV Reactivity by Melt-Recrystallization:

Commercially available TTI based on polymerization of diacetylenes, e.g., that manufactured by Temptime Corporation, Morris Plains, New Jersey, USA are sensitive to UV light. The UV sensitivity of the TTI is not desirable. We screened about 200 different diacetylenes to make precursor TTI. We were surprised to find that many inactive diacetylenes which are sensitive to UV light become significantly less sensitive to UV light when melt-recrystallized. There is no report and we have discovered that diacetylenes which are sensitive to UV light when crystallized from a solution can be made significantly insensitive to UV light by melt-recrystallization. UV sensitivity of diacetylenes prevents their wider utility. Making a diacetylene essentially insensitive to UV light by melt-recrystallization allows wider use of DA based TTI. The insensitivity or low sensitivity of melt recrystallized DA to UV light can be due to formation of DA crystals which are smaller than the wavelength of UV light, i.e., smaller than 200 nm.

It was found that a TTI made from a finely milled powder of a melt crystallized diacetylene, such as 4BCMU (R—C≡C—C≡C—R, where R is $(CH_2)_4OCONHCH_2COO(CH_2)CH_3$), with or without some additives, such as a UV absorber, dispersed in binder solution is significantly less sensitive to UV light than the corresponding TTI made from the same diacetylene from solution with the same ingredients.

Crystal Size and Distribution:

When a diacetylene is crystallized in inactive phase from its solution, usually in a binder by the methods reported in the art (e.g., that in U.S. Pat. Nos. 4,208,186; 4,228,126; 4,276,190; 4,298,348 and 6,524,000), usually there is a very broad distribution of crystal sizes and hence the crystals do not melt fast and do not melt over a narrow range of temperature. Hence, there is a need for a method of making small and inactive crystals (e.g., micron sized or smaller) and of uniform size so that they melt in a narrow temperature range. The hysteresis associated with melting and crystallization of a diacetylene from its melt will be narrower for smaller particles.

Solid Solution Forming Binders:

It was found that some inactive diacetylenes form solid solution with certain polymers when heated above their melting points and cooled. As a result, the thermal reactivity is lower. The diacetylenes do not crystallize because either they recrystallize into inactive phase or form a solid solution with the binder or do not crystallize. Hence, there is a need for a binder which does not substantially form a solid solution with the diacetylene upon cooling.

Molten Diacetylene Becomes a Solvent for the Binder:

When heated above the melting point of the diacetylene, the diacetylene may swell, dissolve, plasticize or partially dissolve some binders/polymers. As a result, the results are not very producible or require precise melting and cooling temperatures and melting and cooling rates. A diacetylene can also slowly crystallize from the solid solution with time and temperature, adding unpredictable additional thermal reactivity. Hence, there is a need for a binder which does not substantially get dissolved, plasticized or swollen with a molten diacetylene.

It was found that a high molecular weight polar binder for a non-polar diacetylene and a high molecular weight non-polar binder for a polar diacetylene usually do not form solid solution or are not significantly affected by each other. Highly crosslinked polymers also do not get readily dissolved with a molten diacetylene. It was also found that polymers which do not melt or dissolve, do not interfere with crystallization of molten DA. As a result, the thermal reactivity of melt-crystallized diacetylene is higher and reproducible.

Converting a Highly Inactive Form of a Diacetylene into Substantially Active Form:

The most preferred diacetylene or cocrystallized diacetylenes is one which is substantially inactive when coated on a substrate and become substantially thermally active and preferably develops color from a few hours to a few months at room temperature or equivalent time at other temperatures.

Use of Solvating Binders:

Solvating binders can be used if the crystals of the inactive diacetylene are very fine and can be melted in very short time, for example, within fraction of a second to a few seconds and crystallized also very fast, e.g., within fraction of a second to a few seconds, so the molten diacetylene does not have time to solvate the binder. Finer crystals also melt faster and at a lower temperature.

Use of a Solid Solvent to Lower the Melting Point and Make Diacetylene Active:

Though lower melting diacetylenes can be used, but a preferred diacetylene suitable for TTI may have melting point higher than 70° C., preferably higher than 100° C. (e.g., 150° C.) so it is not affected by ambient conditions during storage and shipment. If the melting point of the DA is too high, it is difficult to melt activate such diacetylene. Such high melting diacetylenes may require special binders. It is desirable to melt activate the diacetylene around 60° C.-150° C. The melting point of the diacetylene can be depressed by adding either a very high boiling liquid or most preferably a solid, preferably an organic solid compound which depresses the melting point of the diacetylene.

Selection of proper solid solvent for an inactive diacetylene can also help in melt recrystallization of a diacetylene into an active phase in a predictable manner. We found that use of a solid solvent helps many diacetylenes re-crystallize into higher reactivity form and hence can be used to control the reactivity of TTI.

UV Curing Ink as a Binder:

A UV curing binder is a type of radiation-curing ink that cures or sets with the application of ultraviolet light can be used as a binder for making the indicating devices. UV curing ink vehicles are composed of polymerizable fluid oligomers (short chain polymers), monomers (light-weight molecules and that bind together to form polymers), polymer and initiators, that when exposed to ultraviolet radiation, release free radicals (extremely reactive atoms or molecules that can destabilize other atoms or molecules and start rapid chain reactions) that cause the polymerization of the vehicle/binder, which hardens to a dry ink or soft adhesive film containing the ingredient of the coating. UV curing inks are designed to replace heat-set/dried inks whose solvents emit potentially toxic gaseous emissions. The UV curing inks can form an adhesive, soft layer or a very hard and highly crosslinked layer. The words, binder, medium, resin, vehicle, matrix and UV ink or vehicle are used interchangeably herein.

UV curable vehicles, resins and inks for the devices can be mixtures of UV curable acrylate monomers and oligomers, which contain a photo-initiator. For example, the monomeric and oligomeric acrylates can be methyl acrylate, ethyl acrylate, butyl acrylate, ethylhexyl acrylate, hydroxyethyl acrylate, acrylic acid, methyl methacrylate, hexyl methacrylate, beta-phenoxy ethyl acrylate, hexamethylene acrylate, 2-phenoxyethyl acrylate, beta-carboxyethyl acrylate, methoxyethoxyethyl acrylate, glycerol propoxylate triacrylate, hexane diol diacrylate, pentaerythritol tri/tetra acrylate, propoxylated neopentyl glycol diacrylate, trimethylolpropane ethoxy triacrylate, trimethylolpropane triacrylate, tripropylene glycol diacrylate and tetraethylene glycol diacrylate. Classes of UV curable materials that can be used are acrylated and methacrylated alkyls, esters, epoxies and urethanes monomers and oligomers that available from a number of companies, for example, Sartomer, Exton, PA, USA.

Degree of UV curing can be controlled by selecting proper monomer, oligomer, polymer, initiator and UV intensity and exposure time.

Typically, diacetylenes are very sensitive to UV light. However, to make a TTI we initially use inactive form of diacetylenes. Inactive diacetylenes either are totally inactive or have acceptable low UV reactivity. Hence, during UV curing of the binder, the inactive diacetylene either will not develop color or will develop an acceptable low color. Once cured with UV light, the layer containing the diacetylene will be solid, i.e., a precursor TTI. This layer can be heated to melt the inactive diacetylene and recrystallize into an active phase to use as a TTI.

Light Source for UV Curing:

The ink can be cured by IR, visible, UV (long and short), X-ray and electron beam depending upon the photo-initiator and UV curing monomer used. The preferred light source is UV or visible light. The UV light source can be intense LED (light emitting diode). The typical light source spectrum wavelength ranges from ultraviolet light (UVC 200-280 nm, UVB: 280-315 nm, UVA 315-400 nm) to visible light (400-760 nm).

Supported on Neutral Particles & Color Saturation:

Diacetylenes can be supported on or surrounded by neutral, preferably opaque, further preferably porous particles, such as silica, alumina, zinc oxide and micro- or nano-crystalline cellulose. Many other organic and inorganic solid particles can also be used. Supporting DA on an opaque substrate, such as microcrystalline cellulose is a preferred method and offers several advantages: (i) microcrystalline cellulose can be soaked in a solution of a diacetylene, filtered and dried to obtained inactive form of the diacetylene on the opaque particles of cellulose. These particles can be dispersed in a water based binder, a solvent based binder or a UV curing ink, coated on substrate and dried or cured to get a layer of inactive TTI. This method allows one to use a large number of water based, solvent based and UV curing binders, (ii) the effect of thickness of the diacetylene layer on color development will be minimized as after certain thickness, additional thickness will not make the color development darker, (iii) this method also minimizes the diacetylene dissolving or plasticizing the binder as melting will occur either on the surface of the particle or inside the pores of the supporting particles, and (iv) melting and re-crystallization of the diacetylene will be faster and will occur within narrow temperature range. Smaller and high opacity neutral organic and inorganic, preferably white particles are preferred to support, adsorb or adsorb diacetylenes. The melting and recrystallization of diacetylenes will be uniform and reproducible when supporting materials are used. Hysteresis of melt and crystallization will also be much narrower.

The color reference bars for the TTI can be created the same way, i.e., using opaque pigment so effect of thickness and concentration will be minimized. The color reference bars can be created by the conventional method using multi-color and multi-station printing.

Melting Time:

The diacetylene should be melted within a shortest possible time so it does not have time to dissolve, swell or plasticize the binder. However, to quickly melt the diacetylene, the crystals should be smaller and should have narrow size distribution.

Cooling:

In order to obtain reproducible results, the melting/heating and cooling/crystallization of the DA coating should be at the same rate of heating and cooling for all batches. Faster heating or quick melting can be achieved by methods, such as heating with a laser, IR light etc. and rapid cooling or fast crystallization can be achieved by cooling with liquid nitrogen.

Need for Nucleating Agents:

Even though diacetylenes are low molecular weight, there is some possibility of super cooling before they crystallize into an active phase upon cooling. To prevent super cooling there is a need for nucleating agents. Nano and micron sized organic and inorganic materials which do not melt when the diacetylenes melt, can be used to prevent super cooling of molten diacetylenes. It is possible that solid, un-melted additives may act as nucleating agents or if they crystallize before the diacetylene, they can act as nucleating agents.

Nucleating Agents:

Most of the organic and inorganic liquids, including solid melted at high temperatures show super cooling. A variety of nucleating agents are reported in the literature for cloud seeding and freeze indicators. The nucleating agents include, organic, inorganic and biological molecules, such as non-hazardous microorganisms. The most widely used nucleating agents are silver iodide and microorganisms, such as viruses and bacteria including *Pseudomonas* syringe and

*Erminia herbicola*. Microorganism are available from Snomax Inc., York Snow, Victor, NY and Johnson Controls Inc., Milwaukee Wisc.

Need for a UV Absorber:

We were surprised to discover that a number of melt crystallized diacetylenes have very low to essentially no reactivity to both long and short UV light. However, there were some inactive diacetylenes which were still sensitive to prolonged exposure to UV light. Exposure to UV light can give a false positive signal. The effect of UV light can be further minimized or eliminated by adding a UV absorber in the coating formulation and/or by applying a UV absorbing layer on the top of the diacetylene layer. One can also use a UV absorbing aromatic binder, such as polystyrene. UV absorbers listed in U.S. Pat. No. 7,476,874 can be used for the precursor TTI. The disclosures of U.S. Pat. No. 7,476,874 are hereby incorporated in their entirety by reference. We also observed that a melt-activated diacetylene was thermally active but became inactive if exposed to UV light (UV-inactivation). Once top coated UV absorbing layer, the UV-inactivation was stopped.

Aromatic polymers, such as polystyrene, polyethylene terephthalate, aromatic polyurethanes and poly(bis-phenol carbonate) are good UV absorbers. The UV absorbing capability can be further increased and broadened by adding proper UV absorbers, such as benzophenones (hydroxy benzophenones), benzotriazoles (hydroxy benzotriazoles), benzoates, oxanilides and salicylates are widely used as UV absorbers.

Examples of UV absorbers include, benzamide, benzophenone hydrazone, 3,3',4,4' benzophenone tetracarboxylic dianhydride, benzotriazole, 2,2' biphenol, 4,4' biphenol, bisphenol A, 2-(2H-benzotriazole-2-yl-4-methyl phenol), coumarin, ethylhexyl p-methoxycinnamate, 2-ethylhexyl salicylate, oxybenzone, p-aminobenzoic acid its derivatives, diester and/or polyester of a naphthalene dicarboxylic acid, cinnamates (octylmethoxy cinnamate and cinoxate), salicylates (methyl salicylate), anthranilates, such as menthyl anthranilate, 2-ethylhexyl-2-cyano-3,3-diphenyl acrylate, 2-phenyl benzimidazole-5-sulfonic acid, digalloyl trioleate, 3-(4-methyl benzylidene) camphor, 4-isopropyl dibenzoyl methane, butyl methoxy dibenzoyl methane, 2-ethyl-2-cyano-3,3'-diphenyl acrylate, cupferron, ethylsalicylate, hydroxy methoxy benzophenone, hydroxybenzophenone, hydroxycinnamic acid, sulfosalicylic acid, tetrahydroxy benzophenone, fluorescin, fast blue BB, phenothiazine, 4-nitrophenol, 7-hydroxy-4-methylcoumarin, 2-(2H-Benzotriazol-2-yl)-4-(1,1,3,3-tetramethylbutyl)phenol, 2-(2H-Benzotriazol-2-yl)-4,6-di-tert-pentylphenol, Poly[2-(4-benzoyl-3-hydroxyphenoxy)ethyl acrylate], 2-tert-Butyl-6-(5-chloro-2H-benzotriazol-2-yl)$_4$-methylphenol, 2-(2H-Benzotriazol-2-yl)-4,6-bis(1-methyl-1-phenylethyl)phenol, 2,2-Methylenebis[6-(2H-benzotriazol-2-yl)-4-(1,1,3,3-tetramethylbutyl)phenol], 2-(2H-Benzotriazol-2-yl)-6-dodecyl-4-methylphenol, 2-Phenyl-5-benzimidazolesulfonic acid, 2-(2'-hydroxy-5-octylphenyl benzotriazole), 3,4 diaminobenzophenone, 2,4 dihydroxybenzophenone, 3,5 dihydroxy benzoic acid, 2,2' dihydroxy 4,4' dimethyl benzophenone, 2,2' dihydroxy 4 methoxy benzophenone, 2,3 dihydroxy naphthalene, diphenylamine, di-tert-butyl-4-methyl phenol, 4-hydroxybenzophenone, 2-hydroxy-4-methoxy benzophenone, 2-hydroxy-4n-octyloxybenzophenone, lauryl gallate, phenyl hydroquinone, 4,4'(1,4 phenylene diisopropylidine) bisphenol, 4,4'(1,3 phenylene diisopropylidine) bisphenol, salicylanilide, 2,2',4,4'tetrahydroxy benzophenone, 2,3,4 trihydroxybenzophenone, trimethyl hydroquinone, and 1,1,1 tris(4-hydroxyphenyl) ethane.

Solid Solvent:

Some of the inactive diacetylenes have very high melting point, above 100° C., usually about 150° C. Higher melting diacetylene are desirable for TTI but they require heating the device at a much higher temperature. It was found that addition of a neutral solid compound which melts at or below the melting of inactive DA and molten additive has ability to dissolve the molten diacetylenes can help in proper crystallization of diacetylenes into active phases. Solid solvents also help in reducing melting point of diacetylenes, especially when the melting point is high, e.g., above 150° C.

Controlling the Rate of Color Development and the Activation Energy:

Perishables have different shelf lives, varying from about a day to years at room temperature and the activation energy of ~20 kcal/mole to ~60 kcal/mole. Hence, one should be able to control the rate of the color development and the activation energy of the devices. In order to use the current devices for many perishables, one should be able to vary the rate of color development and the activation energy which can be done by varying one or more of the following parameters: nature and concentration of diacetylenes, co-crystallizing with another diacetylenes, rate of cooling/recrystallization, polymerization initiators, inhibitors, additives and binders.

Need for a Non-Melting and Non-Tacky Top Layer:

The heat activated diacetylenic TTI devices reported in the literature cannot be activated by passing through heated roller as the molten diacetylene layer can get stuck on the heated roller. If top coated with a common polymer, the polymer will also melt and can get stuck on the heated rollers. The precursor TTI devices preferably should have a non-stick, non-meltable or a very high melting polymer releasing layer as the top layer or as a binder. The sticking of the precursor TTI on the heated rollers can be prevented by using highly crosslinked acrylate polymer, nonstick polymer, such as Teflon® (polytetrafluoroethylene), crosslinked silicones (polysilicones), polyvinyl alcohol, or laminating with high melting polymer film. Use of the heating-roller coated with Teflon or silicone polymers can minimize sticking of molten precursor TTI. Mold release formulations which are solid can be used for this release layer.

Another way to prevent the precursor TTI from sticking to heated roller during the melt recrystallize process is to apply a non-stick top coat or laminate with a film, such as that of polyethylene terephthalate on the top of the TTI-devices.

The top layer can be created by coating a UV curing formulation as a top coat and curing with a UV light.

Multi-Layered Device:

The current TTI devices will be multilayer devices as shown in FIG. 1. The device can have other layers. The TTI device will be composed minimum of a substrate (e.g., a polymer film, such as PET (polyethylene terephthalate), an indicator layer composed of an inactive diacetylene, a binder, preferably non-solvating binder, optionally a nucleating agent, a UV absorber and other additives and a non-stick, non-meltable top layer. If a paper or porous material is used as a substrate it may require a polymer coat on paper to prevent diffusion of the molten diacetylene and other additives in the porous substrate.

Making the Ink Formulations:

The ink formulation will be composed of a binder, preferably non-solvating to diacetylenes, a solvent, inactive diacetylene and optionally one or more of an initiator/catalyst, a UV absorber, a nucleating agent and other additives. The ink formulation can be made either by the conventional known methods or preferably a single pot method. The conventional method of making the indicator ink formulation is to dissolve the diacetylene and other additives in hot polymer solution and cool to a lower temperature for crystallization of the diacetylene, which can also be used. In one pot method, all reactants and other materials are added in pot to make the ink.

Inactive diacetylene can be obtained by methods, such as crystallization from a proper solvent, by cocrystallization with another diacetylene or an additive and a rapid cooling the formulation for crystallization of the diacetylene in to inactive form. The cooling can be done by passing through a cooling coil or pouring over dry ice or into liquid nitrogen. The selection of a solvent, binder and cooling rate are critical for getting the inactive phase and smaller size of the diacetylene crystals.

Coating Methods:

The coating formulation of precursor TTI can be coated on a substrate by most of the common methods such as flexo, gravure, letter press, inkjet and UV curing, Ranges:

The concentration of the diacetylene in the precursor TTI ink can be from about 5% to about 80%, the preferred concentration is between about 20% and about 50% of the total mass.

The concentration of the binder in the ink can be from about 10% to about 80%, the preferred concentration is between about 20% and about 50% of the total mass.

The concentration of the solvent in the ink can be from about 20% to about 80%, the preferred concentration is between about 20% and about 50% of the total mass.

The concentration of the additives, such as UV absorbers, nucleating agent and other additives can be from about 0.1% to about 40%, the preferred concentration is between about 1% to about 10% of the total mass.

The particle of diacetylenes can be from several nanometers to about 10 micrometers in size. The preferred is about 1 micron.

The melt activation temperature of the precursor TTI will depend on the melting point of the diacetylene. The preferred melting temperature is about 10° C. to about 50° C. above the melting point of the DA. The preferred melting temperature is about 20° C. above the melting point of the DA.

The heating rate will depend upon the melting point of inactive DA and speed of manufacturing. The preferred heating rate to melt activate inactive DA is between about 20° C./second to about 100° C./second. The preferred rate of heating is about 50° C./second.

The cooling rate will depend upon the melting point of inactive DA and the speed of manufacturing. The preferred cooling rate to crystallize the melted DA is between about 20° C./second to about 100° C./second. The preferred rate of cooling is about 50° C./second.

The time required for expiration of activated TTI can be varied from hours to years. The preferred time is about a day to a few months at room temperature or equivalent time at other temperatures.

The activation energy of the activated TTI can be varied from about 10 kcal/mole to about 50 kcal/mole. The prefer activation is energy is about 25±5 kcal/mole.

Inkjet Printing:

Conventional coating and printing methods and equipment, including inkjet printing can be used to make precursor TTI.

Making TTI by Laser Printing:

One can also activate precursor TTI by making toner particles of an inactive diacetylene and melting with melt-fuser of a laser printer. One can create colorless toner particles of an inactive DA using the materials and methods used for making color toner particles. Inactive toner can be made by the traditional method by compounding toner polymer and other ingredients including fine particles of inactive DA and creating large particles, blocks or pieces which then turned into a fine powder by a milling method, such as air jet milling. One can also use improved and recent methods, such as emulsion-aggregation (EA) or chemically prepared toner (CPT) methods. These processes will be composed of aggregation and coalescence of a polymer latex particles with inactive DA particles and other materials, such as wax particles to generate the micron size toner particles. Many polymers are used for making toners, they include styrene acrylate copolymers, polyester resin, styrene butadiene copolymer and a few other special polymers and additives, such as release agent, flow agent, wax and charge control agent. The size of inactive DA toner particles can be from a micron to about 20 microns. The ratio of inactive DA particles to polymer (and additives to make toner) can vary from about 1:1 to about 1:20, preferably about 1:5.

The formation and development of images on the surface of photoconductive materials by electrostatic means, i.e., commonly known as laser printing is well known. The basic electrophotographic imaging process as disclosed in U.S. Pat. No. 2,297,691 describes placing a uniform electrostatic charge on a photoconductive insulating layer known as a photoconductor or photoreceptor, exposing the photoreceptor to a light and shadow image to dissipate the charge on the areas of the photoreceptor exposed to the light, and developing the resulting electrostatic latent image by depositing on the image a finely divided electroscopic toner material. The toner will normally be attracted to those areas of the photoreceptor which retain a charge, thereby forming a toner image corresponding to the electrostatic latent image. This developed image may then be transferred to a substrate, such as paper. The transferred image subsequently may be permanently affixed to the substrate by heat, pressure, a combination of heat and pressure, or other suitable fixing means, such as solvent or over coating treatment. In the course of an electrophotographic printing operation, toner particles are subjected to a number of complex steps, such as charging, electrostatic transfer, fusing, etc.

TTI can be made by laser toner electrophotography technique. The technique of laser printing and manufacturing of toners for laser printing is well developed and widely used. Inactive diacetylene toner can be manufactured by the methods disclosed in art for colored toners. TTI can be made from inactive diacetylene toner using commercially available techniques and equipment.

One of such method is to make inactive DA toner particles by spray drying solution of inactive DA in a suitable binder (e.g., polyacrylate, a polystyrene, a polyester or polymers used as a resin for toner) containing all additives, such as wax, surfactant and surface agents. Dried powder can be further milled, e.g., by air jet milling to obtain micron sized particles. Proper size of inactive diacetylene toner particles can be obtained using materials and methods known in the art. The particle can be further coated with aggregating factor and other surface additives, such as silicon dioxide or silica ($SiO_2$), titanium or titanium dioxide ($TiO_2$) and/or cerium oxide.

Toners and developer compositions including colored particles are well known, for example U.S. Pat. Nos. 5,352,521; 4,778,742; 5,470,687; 5,500,321; 5,102,761; 4,645, 727; 5,437,953; 5,296,325 and 5,200,290. The disclosures of these patents are hereby incorporated in their entirety by reference. In case of inactive diacetylene toner, the colored materials in the above mentioned and other art will be replaced with an inactive DA.

An inactive or precursor diacetylene toner formulation may contains about 50-about 95 weight percent resin/binder, about 2-about 50 weight percent inactive DA, about 0-about 6 weight percent wax, about 0-about 3 weight percent charge control agent, about 0.25-about 1 weight percent flow agent and 0-about 1 weight percent other additives. Widely-used binder's resins, such as styrene-acrylic copolymers, styrene-butadiene copolymers and polyesters can be used as binders to make inactive diacetylene toner.

Precursor/inactive TTI toner particles may also be prepared by appropriate modification of any method within the purview of one skilled in the art, for example, any of the emulsion/aggregation (EA) methods can be user with the polyester resin. However, any suitable method of preparing toner particles may be used, including chemical processes, such as, suspension and encapsulation processes disclosed, for example, in U.S. Pat. Nos. 5,290,654 and 5,302,486, the disclosures of each of which are hereby incorporated by reference in entirety; by conventional granulation methods, such as, jet milling; pelletizing slabs of material; other mechanical processes; any process for producing nanoparticles or microparticles; and so on.

Once inactive DA toner power is made, it can be used as one of the toners in a laser printer modified for making precursor TTI. Laser printer have a fuser to melt toners which will activate the inactive DA into active DA. One can also print the rest of precursor TTI label with other conventional toners to print the instructions and color reference bars.

As a special case, inactive DA particles or inactive DA particles in a binder can be surface coated with a resin and additive to make inactive diacetylene toner.

Monitoring Melt Activation:

We have observed that the coatings of inactive DAs in binders are usually translucent or semi opaque and become nearly transparent when melted and also when crystallized upon cooling. This change in opacity can be used for monitoring activation of inactive DA. One can monitor melting and crystallization of diacetylene in transmission and reflection. As diacetylene crystals are birefringent, one can also use a polarized light for monitoring melting and crystallization of diacetylenes.

Activation Indicator:

The precursor TTI can have a temperature indicator which undergoes an irreversible or reversible color or fluorescence change to confirm that the device is melt-activated. A number of irreversible and reversible color and fluorescence changing temperature indicators are commercially available and they can be used as the activation indicator for precursor TTI devices. Irreversible color changing indicator can also be used to create instructions. Though any temperature indicator can be used, irreversible temperature indicator is preferred, especially that changes from colorless to color or from opaque to clear. The activation of precursor TTI can be confirmed even at high speed with an optical detector/scanner.

The activation indicator can cover entire surface of a precursor TTI device or it can cover only a small area. The activation indicator be on or on the side of the active area of precursor TTI. The activation indicator can undergo two color changes to indicate the range of temperature or a gradual color change to indicate the maximum temperature or temperature range. To demonstrate the concept, we used a coating of a partially polymerized diacetylene [4BCMU, R—C≡C—C≡C—R, where R is —$(CH_2)_4OCONCH_2COO(CH_2)_3CH_3$]. It was blue when coated. It changed to yellow when some precursor TTI melted and became red when cooled.

Activation of a precursor TTI can be monitored by optically, electronically on line.

Un-Activated Indicator Layer:

The un-activated indicator or diacetylene layer is made by coating and drying the ink formulation on a substrate. The substrate may have a sub-layer. Once coated and dried, the indicator layer will be composed of a binder and inactive diacetylene. It may optionally contain a UV absorber, a nucleating agent and other additives.

Activated Indicator Layer:

Precursor TTI device is activated by melting the inactive diacetylene and cooling to a desired temperature. The activated indicator layer will be composed of a binder and melt recrystallized thermally polymerizable diacetylene. It may also contain a UV absorber, a nucleating agent and other additives if added.

Activation of the Inactive TTI Devices:

The inactive TTI device can be activated by melting the inactive diacetylene. Heating can be direct or indirect. The heating of the device to melt the inactive diacetylene can be done many ways, such as blowing hot air, passing between one or more pairs of heated rollers, passing over one or more heated rollers, hot stamping, heating with an infrared (IR) lamp, IR LED lamp or IR laser, ultrasonic, microwave and induction heating. Once the desired temperature is reached, e.g., about 20° C. above the melting point of the diacetylene, the heating should be for a bare minimum time to prevent any degradation of any material and diacetylene dissolving or plasticizing the binder. The heating rate can be slow (e.g., 10° C./minutes) but a very fast heating rate (e.g., 100° C./sec) is preferred. With an IR LED lamp and an IR laser, one can flash very intense beam for a fraction of a second exactly on the indicator to melt the diacetylene. The heating can be very selective to precursor TTI or entire TTI label. One can use a combination of heating methods.

The activation of precursor TTI can be partial or full. The inactive device can also be activated by a thermal printer.

Cooling:

The molten diacetylene need to be cooled for its crystallization into an active phase. The rate of cooling will be determined by the diacetylene, binder and additives in the indicator layer. The cooling rate can be slow (10° C./minute) but a very fast (100° C./second) rate of cooling is preferred. Fast cooling is a preferred method for crystallization of the molten diacetylene. Cooling can be done by blowing ambient or cold air, by passing over a chilled roller or by passing between two chilled rollers.

Activated by Vapor or Two Tape TTI:

Though the most preferred method of activation of the procure TTI is crystallization from melt but the devices can also be activated by exposing to a solvent, such as p-dioxane. The device can also be activated by applying another tape having a PSA containing an activator or a solvent, such as p-dioxane.

Determination of Time Required for a Color Development and the Activation Energy:

The time required for a color development and the activation energy of the activated device can be determined by annealing samples for different periods of time at different temperatures from minus 20° C. to 10° C. below the melting of the diacetylene. Color development can be recorded by scanning the annealed samples or with a time lapsing video camera. The rate of reaction can be determined by plotting the color intensity (e.g., optical density or log of optical density versus time). The activation energy can be determined from the slope of the plot of logarithm of the rate versus reciprocal of the absolute temperature using the Arrhenius equation.

Black Color:

Majority of diacetylenes polymerize to blue, purple and red color. A small number polymerize to orange or yellow color. A small fraction of people is color blind. Hence, the most preferred color of the devices is black. A black color can be obtained by using two or more diacetylenes providing orange/red and purple/blue colors upon polymerization.

Binders:

The preferred binders are natural or synthetic, water or organic solvent soluble, polymers and copolymers, such as polybutylene, polymethylmethacrylate, polybutylmethacrylate, polybutylmethacrylate/isobutylmethacrylate, polyethylene, poly(ethylene-co-acrylic acid), poly(ethylmethacrylate), polyethylene/vinylacetate, poly(isobutylmethacrylate), polyvinylbutyral, polyvinylchloride, polyvinylstearate, poly(ethylene-co-acrylic acid), poly(ethylene-co-methacrylic acid), polybutadiene, polyvinylacetate, poly(ethylene-co-butylacrylate-co-carbon monoxide), poly(o-cresyl glycidyl ether)-formaldehyde, poly(ethyelene-co-1-butene), poly(ethylene-co-methyl acrylate), polyethyiene-co-vinylacetate-co-carbon monoxide), polyhexamethyleneadipate and polyhexamethylenevinylene.

Higher Tg Polymers:

Polymers with high Tg (glass transition temperature) are preferred which include polymers of methacrylic acid, methyacrylonitrile, methacrylic anhydride, methoxystyrene, partially hydrolyzed polyvinyl acetate, polyvinyl butyral, alkyl cellulose, such as methyl cellulose, polymers and copolymers of methyl styrene, phenyl methacrylate, phenyl vinyl ketone, salts of acrylates, salts of methacrylates, acrylates, methacrylates, vinyl alcohol, vinyl acetal, vinyl butyral, and vinyl chloride.

The preferred binders are polyvinyl acetate, polymethylmethacrylate, polyisobutylmethacrylate, polyvinylbutyral, polyvinylchloride, polyacrylics and their copolymers.

Tg of polyacrylic acid and polymethacrylic acid based binders can be increased by neutralization of the acid functionality with organic and inorganic bases.

Substrate:

Any solid substrate can be used as a substrate for the indicating device. Preferred substrate is a flexible plastic film and natural (cellulose) and synthetic (e.g., spun bonded polyolefins, e.g., Tyvek™) papers. Fiber reinforced substrate can be used for sealing tape indicating device. Plastic substrate could be self-colored (pigmented) or coated with a color layer. It could be transparent, semi-transparent, translucent or colored with various intensities. The polymer films include polyolefins (linear or branched), polyamides, polystyrenes, nylons, polyesters, polyurethanes, polysulfones, styrene-maleic anhydride, styrene-acrylonitrile, ionomers based on sodium or zinc salts of ethylene methacrylic acid, polymethyl methacrylates, cellulosics, acrylic polymers (acrylates, such as ethylene methacrylic acid, ethylene methyl acrylate, ethylene acrylic acid and ethylene ethyl acrylate), polycarbonates, cellophane, polyacrylonitriles, ethylene-vinyl acetate and their copolymers can be used as substrate for the devices. The preferred substrates are polyethylene, polypropylene, polyester, cellulose acetate, polyvinyl chloride and their copolymers. These substrates can be metallized.

Particle Size and Milling:

The ink or coating formulation of an inactive DA can also be water based. It can be prepared by several methods, such as (i) emulsifying inactive DA in a water based latex, (ii) melting a low melting inactive DA by heating the latex and the DA and homogenizing the mixture followed by a rapid cooling at a lower temperature and (iii) by mixing fine particles of inactive DA with a polymeric latex. Inactive DA can be milled to fine particles by any conventional method of milling, including air jet milling. The milling can be cryogenic to prevent Inactive DA from melting and coalescence. The size of the inactive DA particles could be from nanometers to several tens of microns, for example, from 10 nm or 100 microns, preferably about a micron. If required, the particle size can be smaller or larger. The fine particles of a precursor TTI can be obtained by many processes, such as conventional methods of milling solids, heating in a medium to dissolve at a high temperature and cooling, especially by rapid cooling to a lower temperature. Commercially available micronization methods, such as milling, bashing and grinding and modern methods, such as spiral jet milling, fluidized bed jet milling, high speed homogenization, jet spraying, and supercritical fluid methods can be used to produce required sized particles of indicator and activators. A large number of polymer latexes are available for printing and coating which can be used as a binder for inactive DA.

One can also disperse the milled inactive DA particles in a solvent based binder as long as the solvent does not dissolve the particles of the inactive DA.

Color Reference Bars Created by UV Light:

We have observed that some of precursor TTI have some low UV sensitivity. Precursor TTI does not develop color upon thermal annealing. Hence, one can create color reference bar by exposing a portion of the precursor TTI to a very high intensity UV light.

High Energy Ionizing Radiation Indicator:

During screening a number of diacetylenes to find right diacetylenes for precursor TTI, we found that some diacetylenes become significantly less thermally and UV reactive when crystallized from melt and still retain the reactivity to gamma/X-ray. Such diacetylenes can be used for monitoring high energy radiation, such as X-ray/gamma ray, electrons, neutrons and protons.

Precursor TTI Made by Inkjet Printing:

It is also possible to make precursor TTI by inkjet printing from the dispersion of inactive diacetylenes in a vehicle/binder system for inkjet ink. Dispersions of inactive TTI can be prepared in water and solvent based binders using the procedures and diacetylenes disclosed herein. Precursor TTI and visitors' badges can be prepared by printing desired shapes (e.g., squares or circles) and words (e.g., Expired) using the technology of inkjet printing. The precursor TTI can be activated by the melt activation methods disclosed herein.

Precursor TTI in Form of Barcode or on a Barcode:

One can also print the precursor TTI which develops blue color in form of barcode on a substrate. After the melt-activation, the barcode will become readable with time and temperature of annealing. One can also coat the dispersion of precursor TTI which develops blue color upon melt activation on blue-and-white or black-and-white barcode. The blue-and-white and black-and-white barcodes coated with precursor TTI formulation will become non-readable with time and temperature after the melt activation.

Process of Reading with I-Phone:

It is also possible to read the melt-activated precursor TTI with cell phones/I-phones having such capability.

Color Reference Bars with Varied Intensity:

In order to determine the expiration, the TTI can have one or more color reference bars adjacent to the TTI.

Packaging Tape TTI:

The precursor TTI can be in form of a packing tape. Packaging tape precursor TTI will be composed of a long substrate having an adhesive, such as a hot melt adhesive or a pressure sensitive adhesive (PSA) and a release liner on one side and a coating of precursor TTI on the other side. The width of the packing tape TTI can be from 1 cm to 10 cm or larger if required. The packaging tape precursor TTI is melt activated and applied on a package/box of perishables.

Milling with Additives:

One can also prepare a dry powder of an inactive diacetylene and additives from their solution and mill into fine powder (e.g., about a micron). The milled powder can be dispersed in a water or solvent based binder and coated on a substrate to make a precursor TTI. With proper additives, this powder can also be used as toner.

Conventional Method of Making DA-TTI:

Diacetylenes have many desired properties, such as the reaction (polymerization—color development) occurs in the solid state, a one reactant system, one ink formulation, one layer/coating device, paper can be used as a substrate and no effect of humidity.

The major steps of the conventional method of making DA-TTI are:

Synthesize DA and keep cold.

Mill the DA at low temperature,

Make an ink from milled DA, binder, solvent and additives. Keep cold.

Make lab prototype and determine thickness of the coating required and kinetics.

Run a pilot trial, check calibration, coating thickness & expiration color reference chart etc.

Make a small production run for assurance of the calibration/quality of the product.

Manufacture the TTI using the same conditions, such as web speed and drying, . . . etc.

Keep the product very cold/frozen.

Check the calibration. If OK release the product.

Ship the product cold.

Receiving party keeps the product cold till used.

In summary, the conventional methods of making DA based TTI require highly trained, skilled labor force for lab and pilot trials and calibration at every stage, expensive equipment for manufacturing, protection of UV light and cold storage from start to finish. Thus, the method is expensive, complex, tedious and problematic.

Steps and Procedures of Making Precursor TTI Devices:

The following is an outline of the steps to be taken to make the TTI devices from inactive DA:

Select diacetylenes, additives and other materials required for the device.

Synthesize diacetylene and make the inactive indicator ink. The ink may have additives, such as UV absorber and nucleating agent. The diacetylene and the ink being inactive can be stored for months or years at room temperature and under ambient light.

Coat the inactive indicator ink of the DA on a substrate having a PSA layer and release liner on the back. In contrast to an ink of an active diacetylene, the ink of inactive DA can be dried by blowing hot air below the melting point or dissolution of the diacetylene. The substrate can be in form of a roll or sheets.

Apply a UV absorption layer on the indicator layer. This UV layer can be coated at the end as a top coat as well. As the diacetylene is inactive, the coated roll can be stored under ambient conditions for a very long time, for example, months and years. This gives ample time for printing color reference bars, instruction and calibration of the devices. It also eliminates the need for cold storage. Active diacetylenic TTI require cold storage once coated/made.

Select samples randomly and melt activate using a set of pre-calibrated heated rollers.

Anneal samples for different periods at different temperatures.

Determine the activation energy and select a color shade for expiration reference bar.

Prepare printing plates to print color of the expiration reference bar and any instructions.

Reload the inactive DA (precursor TTI) roll and print the color reference bar and a non-melt/stick coat or laminate with a plastic film which has either very melting or softening point or highly crosslinked. Die cut the roll into indicators stickers.

Randomly select the samples and confirm the expiration time and the activation energy. This device allows the manufacturer ample time to confirm the calibration and performance of the indicators.

The roll of the indicator stickers can be stored for months and years under ambient conditions and can be shipped to the users under ambient conditions. The active diacetylene TTI require cold storage and shipment till used.

Activate the inactive TTI by passing through a calibrated heated roller or any other heating system to melt and pass through chilled rollers (or similar cooling system) for crystallization of the diacetylene. Apply the activated TTI labels on perishable containers or store the roll at a lower temperature, e.g., below minus 30° C. till ready to be used.

The device will require a non-tacky coating, high melting or non-melting over coat so that the device does not stick to heated rollers during the activation. The device optionally can have an irreversible color changing indicators to monitor activation of the device. If properly activated, the indicator will change color. As the coating of the precursor TTI undergoes change in optical density (from semi-opaque/translucent to almost clear/transparent, the melt activation can be monitored by monitoring change in opacity of the device.

In summary, precursor TTI ink is made in one pot and in one continuous procedure. No need for cold storage of DA or ink. It eliminates multi-step procedures of synthesis of DA & making ink. It is simple, safe, reliable, faster, least problematic and less overhead which lower the cost. The inactive TTI is made by coating the ink on a substrate and a top UV absorbing coat (optional). No effect of ambient conditions (including UV light) and can be stored for years at room temperature. Huge saving as no cold storage and no frequent calibrations required, just activate and supply/apply. Expiration color chart and instructions are printed around the inactive TTI, a non-stick top coat is applied and labels are die-cut. The inactive TTI can be stored for years at room temperature, a huge saving. Activate the TTI by quick melting and cooling the inactive TTI (by passing over heated and chilled rollers respectively) and apply on perishables. Precursor TTI and methods have fewer steps, are reliable, not sensitive to UV light, no cold storage/shipment and low cost and no problems of the conventional methods.

Self-Activating, Tamper Evident, Heat Shrinkable Seal/Band Precursor TTI:

Heat shrinkable bands and seals are used on the caps and lids of containers of perishables as tamper evident. If these bands are coated with a precursor TTI formulation, the precursor TTI will get automatically activated only when heat sealed, thereby providing both a temper indicator and a TTI simultaneously. We coated a precursor TTI ink formulation of a diacetylene (2PmCl, R—C≡C—C≡C—R, where R=$(CH_2)_2$—O—CO—NH-m-chlorophenyl, see Example 6) on a heat shrinkable tube and dried. The band was placed on vial and heat sealed. A portion was not heated enough to melt the diacetylene. The band tightly sealed the vial cap and the inactive coating upon melting changed from opaque to clear. The vial was placed in an oven at 70° C. and photographed at different time. FIG. 5 show the photos of the heat seal TTI taken at different times. The band can have an expiration color reference bar. The precursor TTI band developed purple color and the color intensified with time and temperature. This tamper evident, heat shrinkable, precursor TTI band has advantages of both the tamper evident heat shrinkable band and TTI with disadvantages of none. It offers many advantages including:

No additional special equipment (e.g., label applicator or heater) are required as the inactive precursor band will self-activate when the bend is heat shrunk.

The temperature of heat shrinking of the band and melt activation temperature of the band can be matched by selecting proper inactive DA formulation. Many inactive DA have melting point (melt activation temperature) from ~80° C. to 160° C. to match the heat shrinking of the band.

Activated TTI is easily noted as one has to break the seal to use the perishable, compared to a TTI on a label.

Thermally-Printable, Self-Expiring, Self-Activating TTI and Visitors' Badges:

Visitors' badges are widely used to keep record of the visitors. Thermally printed visitors' badges are also widely used but they are not self-expiring. Commercially available self-expiring visitors' badges which when activated change color with time. These self-expiring visitors' badges are actually time-temperature indicators based on diffusion of a dye which require manual activation when issued.

Precursor TTI is very similar to the thermally coated paper that both are thermally activated except that the color development of the thermal coating is instant while that of the precursor TTI is with time and temperature. Using the inactive DA, one can create thermally-printable, self-expiring, self-activating visitors' badges and TTI. Thermal printing (coated paper and printer) technology is well developed, inexpensive and very widely used. There are many ways to create thermally-printable, self-expiring, self-activating visitors' badges and TTI from inactive DA. Three of them are described below.

Method 1: A paper or plastic film is coated with a conventional thermally activated coating except for a small area where inactive DA is coated. Using a thermal printer and a software, one can print information in black and white on the thermal coating and activate the inactive DA coating simultaneously as shown schematically in FIG. 6. The melt-activated DA will slowly develop color with time. If a color reference bar is printed adjacent to inactive DA coating it will indicate when the badge expires when the inactive DA coating is darker than the color reference bar. A label for a perishable with TTI can be created in a similar way.

Method 2: A thin sticker having a coating of an inactive DA and a color reference bar on an opaque substrate is placed on a thermal paper. The area under the sticker can be without any thermal coating. Using a thermal printer and a software, one can print information in black and white on the thermal coating and activate the inactive DA coating of the sticker simultaneously as shown in FIG. 7. The melt-activated DA will slowly develop color with time and temperature. The badge will indicate expiration when the activated DA coating is darker than the color reference bar.

Method 3: A substrate, such as paper or plastic film coated with inactive DA on one side and an adhesive and a release liner on the other side can be activated with a thermal printer and used as a TTI and a self-expiring visitor's badge. An example of this method is shown in Example 7 and in FIG. 8.

Advantages:

The current system of melt activation of inactive diacetylenic TTI offers many advantages over other TTI, especially TTI based on active diacetylene including:

This system can provide TTI as good as that made from active diacetylene without the need for the cold storage and shipment.

The system will be much less expensive and easier to manufacture.

It has advantages of activation of the two-tape devices (e.g., those reported in U.S. Pat. Nos. 5,053,339 and 8,343,437) and that of active diacetylene TTI (U.S. Pat. No. 3,999,946, commercially available from Temptime Corporation, Morris Plains, NJ) with disadvantages of none.

Printed inactive indicators can be stored for a long time under ambient conditions which eliminates the need for cold storage.

The indicator ink can be stored under ambient conditions and inactive TTI can be made by drying with hot air using hot air and hence conventional equipment can be used.

The system provides sufficient time for calibration and validation of the system.

It is not affected by UV light.

It can be used for a large number of other perishables as no cold storage required, no UV sensitivity and can be activated onsite.

A paper can be used as a substrate (paper is a substrate for most perishable labels).

TTI orders can be delivered very fast (orders can be filled in matter of days compared to months); just activate and ship cold or let customers activate the precursor TTI.

It can also be pre-activated and shipped cold similar to DA based TTI of Temptime Corporation.

Tamper evident, self-activating, heat shrinkable seal/band TTI can be made.

Thermally-printable, self-expiring, self-activating TTI and visitors' badges and TTI can be made.

EXPERIMENTAL

Example 1: TTI Device with Induction Period

Diacetylene 1pTS (R—C≡C—C≡C—R, where R=$CH_2$—O—$SO_2$-p-tolyl) was synthesized according to procedure disclosed in U.S. Pat. No. 3,999,946. In a test tube, 0.5 g of 1pTS was dissolved in 5 g of 10% solutions of polyepichlorohydrin in toluene. The solution was heated near boiling and cooled rapidly to ~5° C. After 15 minutes the resultant mixture, nearly white suspension was brought to room temperature. The suspension was coated on a polyester film using a four mil (100 microns) Bird type film applicator. A portion of the coatings was coated with a commercially available water based UV absorbing ink. The coating was placed in an oven and dried for 15 minutes by raising the temperature ~60° C. The coating was translucent (slightly white). The coating thickness was about 1 mil (25 microns). A portion of the coating was melted by letting the non-coated side of the substrate touch a heated (about 130° C.) roller of a laminator. The coating melted almost instantly and changed to almost transparent. The melted portion was immediately cooled to room temperature. The melt-recrystallized and un-melted portions were cut into small strips and the strips (i) exposed to 254 nm UV light and (ii) annealed in ovens at 50° C. and 80° C.

UV Exposure Results:

The melt-recrystallized and UV coated portions developed barely noticeable faint red color but the un-melted developed easily noticeable red color upon exposure to 254 nm UV light from a 40-watt lamp (Ushino G1578, Japan) at 30 cm for about 10 minutes.

Annealing Results:

Un-melted and melt-recrystallized portions were annealed at 50° C. and 80° C. The un-melted portions did not develop color but the melt-recrystallized portions developed red color. The red color intensified with time and changed to brown black after 1 day at 50° C. The color change from red to brown/black occurred within 30 minutes after about 5 hours at 80° C. The results indicate that 1pTS has a long induction period of polymerization, i.e., color change from red to brown black within 20% of the total time.

Example 2: 1mTU (Gradual Color Change)

Diacetylene 1mTU (R—C≡C—C≡C—R, where R=CH$_2$—O—CO-m-tolyl) was synthesized according to general procedure disclosed in U.S. Pat. No. 4,276,190. In a test tube, 0.5 g of 1mTU was dissolved in 5 g of 10% solutions of polyepichlorohydrin in toluene. The solution was heated near boiling and cooled rapidly to ~5° C. After 15 minutes the resultant mixture, nearly white suspension was brought to room temperature. The suspension was coated on a polyester film using a four mil (100 microns) Bird type film applicator. The coating was dried in an oven at about 50° C. for 15 minutes. The coating was translucent light beige color. A portion of the coatings was coated with a commercially available water based UV absorbing ink. The coating thickness was about 1 mil (25 microns). A portion of the coating was melted by letting the non-coated side of the substrate touch a hot (about 130° C.) roller of a laminator. The coating melted almost instantly and changed to almost transparent and faint orange. The melted portion was immediately cooled to room temperature. The melt-recrystallized and un-melted portions were cut into small strips and the strips were (i) exposed to 254 nm UV light and (ii) annealed in ovens at 50° C. and 80° C. for 1 day.

UV Exposure Results:

The melt-recrystallized and UV coated portions did not develop color but the un-melted developed orange color upon exposure to 254 nm UV light from a 40-watt lamp (Ushino G1578, Japan) at 30 cm for about ten minutes.

Annealing Results:

The melt-recrystallized portions annealed at 50° C. and 80° C. for 1 day developed orange red color. The color of the samples annealed at 80° C. was darker than that annealed at 50° C.

Example 3: Effect of Binders

Inactive dispersions of a diacetylene, 2PmCl (R—C≡C—C≡C—R, where R=(CH$_2$)$_2$—O—CO—NH-m-chlorophenyl) was prepared in different polymeric binders such as polyvinyl acetate, polyisobutylmethacrylate, polystyrene, polyvinyl chloride, chlorinated rubber and polyvinyl butyral using the general procedure of Example 1. The dispersions were coated on polyester films to get ~25 micron dry coatings. Narrow (~1 cm) strips were cut from the coatings. A portion of the coatings of the strips was melted on heated (140° C.) roller of a laminator while the remaining portion was kept un-melted. The strips (with molten and un-molten portions) were annealed at 80° C. for different periods of time. The un-melted portion developed negligible color but the melt activated portions developed blue purple color with time and temperature as shown in FIG. 2.

Effect of UV absorber and UV light: A strip was coated with a commercially available UV absorber. One side of the UV coated and un-coated strips were melted by letting the non-coated side of the substrate touch a hot (about 130° C.) roller of a laminator. The coating melted almost instantly and changed to almost transparent. The melted portions were immediately cooled to room temperature. The strips exposed to 254 nm UV light from a 40-watt lamp (Ushino G1578, Japan) at 30 cm for about one hour. The results are shown in FIG. 3. The un-melted portion developed a slight purple color, however, the melted portions and UV coated portions did not develop any color after the prolonged exposure to intense UV light. The thermal reactivity of melt activated TTI depend upon several parameters, such as nature of the polymer, melting temperature, rate of heating and cooling and concentration of diacetylene.

Example 4: Controlling Color and Thermal Reactivity by Co-Crystallization of Two Diacetylenes Two diacetylenes, 2PmCl (R—C≡C—C≡C—R, where R=(CH$_2$)$_2$—O—CO—NH-m-chlorophenyl and 1PmCl (R—C≡C—C≡C—R where R=CH$_2$—O—CO—NH-m-chlorophenyl) were mixed in varied proportions (1:0, 0.8:0.2, 0.6:0.4, 0.4:0.6, 0.2:0.8 and 0:1). The dispersions of the mixtures were obtained using the general procedure of Examples 1 and 2. The dispersions were coated on polyester films to get ~25 micron dry coatings. A portion of the coatings was coated with a commercially available water based UV absorbing ink. Narrow (~1 cm) strips were cut from the coatings. A portion of the coatings of the strips was melted on a heated (140° C.) roller of a laminator while the remaining portion was kept un-melted. The strips, (i) with molten and un-molten portions and (ii) un-coated and coated with a UV absorbing ink, were annealed at 80° C. for 16 hours and also exposed to UV lamp [a 40 watt, 254 nm UV lamp (Ushino G1578, Japan) at 30 cm] for one hour. The un-melted portion developed blue or red color depending cocrystallized formulation but the UV coated and molten portions (UV coated or not) did not develop color upon a prolong exposure to UV light. The molten portions developed, essentially the same color upon thermal annealing.

The results show that (i) the color, the UV reactivity and the thermal reactivity of a diacetylene can be controlled by cocrystallization with another diacetylene (ii) the UV reactivity can be substantially reduced, almost eliminated upon melt activation of a diacetylene and cocrystallized diacetylenes, (iii) the thermal reactivity can be significantly increased by melt recrystallization, and (iv) the UV reactivity of un-activated and activated diacetylene can be further minimized by applying a UV absorbing layer.

Example 5: Precursor TTI Made by Solution and Milling Methods

5A—Solution Method: Diacetylene 1PU (R—C≡C—C≡C—R where R=$CH_2$—O—CO—NH—phenyl) was synthesized according to general procedure disclosed in U.S. Pat. No. 4,276,190. In a test tube, 0.5 g of 1P was dissolved in 5 g of 10% solutions of polyepichlorohydrin in toluene. The solution was heated near boiling and cooled rapidly to ~5° C. After 15 minutes the resultant, nearly white suspension was brought to room temperature. The suspension was coated on a polyester film using a four mil (100 microns) Bird type film applicator. The coating was dried in an oven at about 50° C. for 15 minutes. The coating was translucent white. The coating thickness was about 1 mil (25 microns). A portion of the coating was melted by letting the uncoated side of the substrate touch a hot (about 130° C.) roller of a laminator. The coating melted almost instantly and changed to almost transparent and faint yellow. The melted portion was immediately cooled to room temperature. The melt-recrystallized and un-melted portions were (i) exposed to 254 nm UV light and (ii) annealed in ovens at 50° C. and 80° C.

UV Exposure Results:

The melt-recrystallized portion developed light red color but the un-melted developed much darker red color upon exposure to 254 nm UV light from a 40-watt lamp (Ushino G1578, Japan) at 30 cm for about ten minutes.

Annealing:

The melt-recrystallized and un-melted portions annealed at 50° C. and 80° C. for 1 day developed red color. The un-melted portions did not develop color. The melt-recrystallized portions developed red color. The samples annealed at 80° C. were darker than that annealed at 50° C.

5B—Milling Method: Solvent crystallized PU was milled into a very fine powder in a vibratory ball mill. The milled powder was dispersed in 10% solution of polyepichlorohydrin in a mixture of toluene and cyclohexane and in Joncryl 77 (a water based polyacrylic resin from Bayer AG) with high speed homogenizer to make 1:1 diacetylene to binder ratio. The dispersions were coated on a polyester film to get about 1-4 mil dry coatings. A portion of the coatings ware melted by letting the backside of the coating touch a hot (about 130° C.) roller of a laminator. The coating melted almost instantly and changed to almost transparent and faint yellow. The melted portion was immediately cooled to room temperature. The melt-recrystallized and un-melted portions were (i) exposed to 254 nm UV light and (ii) annealed in ovens at 50° C. and 80° C. The results were essentially the same as that of Example 5A.

Example 6. Making of a Self-Activating, Tamper Evident, Heat Shrinkable Seals/Bands Precursor TTI A heat shrinkable tube was dipped in an inactive dispersion of a diacetylene, 2PmCl (R—C≡C—C≡C—R, where R=$(CH_2)_2$—O—CO—NH-m-chlorophenyl) and dried. The coated heat shrinkable tube placed on a vial and heated with a hot air to melt a portion. The vial was annealed at 70° C. for different periods. The melt activated portions of the coating developed blue violet color and the color intensified with time and temperature as shown in FIG. 5.

Example 7. Activation of Precursor TTI with a Thermal Printer

An inactive dispersion of a diacetylene (3E16, R—C≡C—C≡C—R, where R=$(CH_2)_3$OCO$(CH_2)_{14}CH_3$) was obtained by using the general procedure of Examples 1 and 2. The dispersion was coated on a polyester film and dried in oven to get ~25 microns thick coating. The diacetylene coating was top coated with Joncryl77 (an acrylic latex of BASF) and dried to make a precursor TTI and visitors badges. Proper sized pieces of the coated film were inserted in a DYMO LabelWriter (model 450) thermal printer instead of the normal thermal printer labels. Different shapes (e.g., square and circle) and words (e.g., "JPL LABS" and "Expired") were created on the films with the thermal printer. The shapes and characters were not visible or barely visible as shown in FIG. 8A. Red color printing started appearing and the color of the printing intensified with time and temperature. The printing was clearly readable after a day at room temperature and within a few hours in an oven at 60° C. The unprinted areas were colorless/white as shown in FIG. 8B.

The pieces of the film were also activated by passing through a laser printer (Brother MFC) with and without any toner printing. The heat fuser of the laser printer melted the coating and made it thermally active. The melt activated coating developed red color with time and temperature.

The pieces of the film were also passed through heated rollers of a laminator. The coating got activated and developed red color with time and temperature of annealing.

The results clearly indicate that one can make TTI and visitors' badges from DA based precursor TTI by activating with a thermal printer.

The invention claimed is:

1. A precursor time-temperature indicating (TTI) device composed of a substrate having thereon:
   a color changeable diacetylenic layer composed of at least one binder, particles of at least one diacetylene and a UV absorber;
   a UV absorbing layer; and a release layer on the color changeable diacetylenic layer;
   wherein the diacetylene is inactive thermally and in UV prior to melt recrystallization and becomes thermally active with increased thermal reactivity to develop color with time and temperature upon melt recrystallization.

2. The precursor TTI device of claim 1 wherein at least one layer undergoes a visual or machine readable change including change in opaqueness, transparency, color or fluorescence when the inactive diacetylene is melt recrystallized.

3. The precursor TTI device of claim 1 having at least one color reference bar for monitoring expiration of a perishable by matching its color with the color of the color changeable layer when the diacetylene is melt recrystallized.

4. The precursor TTI device of claim 1 wherein the release layer is composed of the group consisting of one or more materials selected from polysiloxane, a silane, a polysilicone, a fluorosilicone, polyvinyl alcohol, polytetrafluoroethylene and a crosslinked polymer.

5. The precursor TTI device of claim 1 wherein one or more diacetylenes are selected from the group consisting of R—C≡C—C≡C—R, where R is selected from: $(CH_2)_b$—H; $(CH_2)_b$—OH; $(CH_2)_b$—OCONH—R1; $(CH_2)_b$—O—CO—R1; $(CH_2)_b$—O—R1; $(CH_2)_b$—COOH; $(CH_2)_b$—COOM; $(CH_2)_b$—NH_2$; $(CH_2)_b$—CONHR1; $(CH_2)_b$—NHCONHR1; $(CH_2)_b$—CO—O—R1; where b=1-10, and R1 is substituted or unsubstituted alkyl or phenyl where the substituent group is a alky or phenyl group, with or without one or more substituents selected from the group of —Cl, —Br, —I, —F, —NO$_2$, alkyl, phenyl, alkoxy and phenoxy; and M is a cation; and their cocrystallized mixtures.

6. The precursor TTI device of claim 5 wherein said cation is selected from the group consisting of Na$^+$ an (R1)$_3$N$^+$.

7. The precursor TTI device of claim 5 wherein said b is 1-4.

8. The precursor TTI device of claim 1 wherein the particles of the diacetylene are obtained by milling the diacetylene or by rapid cooling of the diacetylene from its solution.

9. The precursor TTI device of claim 1 which has a shelf life of a week to a decade at room temperature without development of any noticeable change including change in color.

10. The precursor TTI device of claim 1 wherein the device is activated by heating the diacetylenic layer from room temperature to above the melting point of the diacetylene in seconds or less and cooled to room temperature from the molten state in seconds or less.

11. The precursor TTI device of claim 1 wherein the diacetylene is melted by passing over at least one heated device and crystallized from the molten diacetylene by passing over a cooling device.

12. The precursor TTI device of claim 11 wherein said heated device is selected from the group consisting of a heated roller, blowing hot air, an infrared light and induction heating.

13. The precursor TTI device of claim 11 wherein said cooling device is selected from the group consisting of a cooled roller and blowing cold air.

14. The precursor TTI device of claim 1 wherein the substrate is a heat shrinkable plastic tubing.

15. The precursor TTI device of claim 1 which can be activated by melting the diacetylene with a thermal printer.

16. An apparatus for melt activation of the precursor TTI device of claim 1 composed of at least one heating device to melt the diacetylene and at least one cooling device to cause crystallization of the molten diacetylene.

17. A process of making a TTI device comprising:
heating the precursor TTI device of claim 1 above the melting point of the inactive diacetylene; and
(i) cooling the heated precursor TTI device to below the melting point of the diacetylene to obtain a melt recrystallized diacetylene.

18. The process of claim 17 wherein the device is heated to about 10° C. to 30° C. above the melting point of the inactive diacetylene.

19. The process of claim 18 wherein the heated device is cooled to room temperature or below.

20. A process of activation of device of claim 1 comprising melting the device above the melting point of the diacetylene and then cooling the device below the melting point of the diacetylene.

21. The precursor TTI device of claim 1 which is activated by a thermal printer to make a time temperature indicator or a visitor's badge.

22. The precursor TTI device of claim 1 further comprising one or more additives selected from a UV absorber, a melting point depressor, a nucleating agent, a release agent and opaque particles.

23. The precursor TTI device of claim 1 further comprising at least one layer selected from a UV absorbing layer, an adhesive layer, a protective layer and a release layer over the color changeable diacetylenic layer.

24. The precursor TTI device of claim 1 further comprising at least one of a melting point depressor, a nucleating agent, a release agent and opaque particles.

* * * * *